US011517194B2

(12) United States Patent
Chen et al.

(10) Patent No.: US 11,517,194 B2
(45) Date of Patent: Dec. 6, 2022

(54) OPTICAL BIOPSY APPLICATORS FOR TREATMENT PLANNING, MONITORING, AND IMAGE-GUIDED THERAPY

(71) Applicant: The Regents of the University of California, Oakland, CA (US)

(72) Inventors: Zhongping Chen, Irvine, CA (US); Yusi Miao, Irvine, CA (US); Yan Li, Irvine, CA (US); Bruce J. Tromberg, Irvine, CA (US); Yona Tadir, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1013 days.

(21) Appl. No.: 16/235,426

(22) Filed: Dec. 28, 2018

(65) Prior Publication Data

US 2019/0200851 A1    Jul. 4, 2019

Related U.S. Application Data

(60) Provisional application No. 62/611,990, filed on Dec. 29, 2017.

(51) Int. Cl.
*A61B 1/303* (2006.01)
*A61N 5/06* (2006.01)
(Continued)

(52) U.S. Cl.
CPC .......... *A61B 1/303* (2013.01); *A61B 1/00082* (2013.01); *A61B 1/00172* (2013.01);
(Continued)

(58) Field of Classification Search
CPC . A61B 1/303; A61B 1/00082; A61B 1/00172; A61B 1/00188; A61B 1/043;
(Continued)

(56) References Cited

U.S. PATENT DOCUMENTS

2011/0098572 A1* 4/2011 Chen .................... A61B 5/0062
600/463
2011/0282192 A1* 11/2011 Axelrod ............... A61B 5/0066
600/427

(Continued)

OTHER PUBLICATIONS

Tadir, Y. Light and Energy Based Therapeutics for Genitourinary Syndrome of Menopause: Consensus and Controversies. Laser Surg. Med. 2017;49(2), 137-159.

*Primary Examiner* — Joseph M Santos Rodriguez
*Assistant Examiner* — Kaitlyn E Sebastian
(74) *Attorney, Agent, or Firm* — Nguyen Tarbet LLC

(57) ABSTRACT

An in vivo optical biopsy applicator of the vaginal wall for treatment planning, monitoring, and imaging guided therapy is described herein. The applicator may include an imaging probe operatively coupled to a laser ablation device. The applicator allows for non-invasive optical tissue monitoring in order to define pre- and post menopausal parameters, pre- and post-treatment microscopic changes, and offers an objective scientific tool in order to compare currently available medical, non-medicated, and energy-based treatment protocols.

12 Claims, 20 Drawing Sheets
(12 of 20 Drawing Sheet(s) Filed in Color)

(51) Int. Cl.
*A61B 1/00* (2006.01)
*A61B 1/06* (2006.01)
*A61B 1/07* (2006.01)
*A61B 8/12* (2006.01)
*A61B 8/00* (2006.01)
*A61B 1/04* (2006.01)
*A61B 5/00* (2006.01)
*A61N 5/067* (2006.01)

(52) U.S. Cl.
CPC .......... *A61B 1/00188* (2013.01); *A61B 1/043* (2013.01); *A61B 1/063* (2013.01); *A61B 1/07* (2013.01); *A61B 5/0066* (2013.01); *A61B 5/0095* (2013.01); *A61B 5/4318* (2013.01); *A61B 5/4836* (2013.01); *A61B 8/12* (2013.01); *A61B 8/445* (2013.01); *A61N 5/0603* (2013.01); *A61B 5/0035* (2013.01); *A61N 5/067* (2021.08); *A61N 2005/0611* (2013.01); *A61N 2005/0666* (2013.01)

(58) Field of Classification Search
CPC ......... A61B 1/063; A61B 1/07; A61B 5/0066; A61B 5/0095; A61B 5/4318; A61B 5/4836; A61B 8/12; A61B 8/445; A61B 5/0035; A61B 8/4416; A61N 5/0603; A61N 5/067; A61N 2005/0611; A61N 2005/0666

See application file for complete search history.

(56) References Cited

U.S. PATENT DOCUMENTS

| | | | |
|---|---|---|---|
| 2012/0080612 A1* | 4/2012 | Grego | G02B 26/101 |
| | | | 29/25.35 |
| 2014/0088571 A1* | 3/2014 | Loeb | A61B 18/24 |
| | | | 606/3 |
| 2015/0351722 A1* | 12/2015 | Chen | A61B 8/12 |
| | | | 600/427 |
| 2016/0206373 A1* | 7/2016 | Chen | A61B 5/0084 |
| 2016/0317226 A1* | 11/2016 | Jagdeo | A61B 90/06 |
| 2016/0374562 A1* | 12/2016 | Vertikov | A61B 5/0095 |
| | | | 600/424 |
| 2017/0181889 A1* | 6/2017 | Abe | A61B 18/042 |

* cited by examiner

VE: vagina epithelium, LP: lamina propria

VE: vagina epithelium, LP: lamina propria, T: transudate

VE: vagina epithelium, LP: lamina propria, A: ablated tissue

OPTICAL BIOPSY APPLICATORS FOR TREATMENT PLANNING, MONITORING, AND IMAGE-GUIDED THERAPY

CROSS-REFERENCES TO RELATED APPLICATIONS

This application is a non-provisional and claims benefit of U.S. Provisional Application No. 62/611,990 filed Dec. 29, 2017, the specification(s) of which is/are incorporated herein in their entirety by reference.

GOVERNMENT SUPPORT

This invention was made with government support under Grant No. P41EB-015890, FG18869 (443810/29873), awarded by NIH. The government has certain rights in the invention.

FIELD OF THE INVENTION

The present invention relates to an apparatus for monitoring vulva-vaginal and uro-genital wall, examining histology and histopathology during and following any kind of medical, hormonal, lubricant, and energy-based therapeutics using radiofrequency, fractional, scanning, or pixel-printing laser probes that are integrated into an energy-based therapeutic probe.

BACKGROUND OF THE INVENTION

Pelvic floor disorders, including vulvo-vaginal atrophy (VVA), vaginal laxity, pelvic organ prolapse and urinary incontinence, termed sometimes as genito-urinary syndrome of menopause (GSM), are very common conditions that can significantly affect a patient's quality of life and are especially challenging disorders for clinicians to predict and treat. Pelvic organ prolapse and urinary incontinence occurs in 3 of 10 vaginal deliveries and affects up to half of women older than 50 years. These are among the most common indications for gynecologic surgery.

The number of surgeries for various degrees of pelvic floor disorders and the expense of the healthcare system as a result will continue to rise because of the natural growth of the elderly population. Due to the complexity of pelvic floor conditions, experts specializing in this field have developed an increasingly advanced diagnostics and surgical techniques and skills, and more frequently using evolving technologies such as imaging in the diagnosis and treatment of those conditions. Despite the advancement in this field, the current understanding remains limited of the physiology and pathophysiology that underlines vaginal dryness, pelvic floor weakness and urinary incontinence.

Current imaging technologies focus on ultrasound and MRI. However, very few information can be obtained about the surface anatomy and histology that is part of the early stage development of pelvic floor disorders. In addition, those imaging technologies are limited by the size and cost of examination, and not suitable for routine monitoring. Moreover, since most of the pelvic floor changes are considered age and hormonal status related, invasive tissue biopsies are not justified and the pathophysiology is not studied in-depth. Understanding the anatomic causes of aging and childbirth injury or other types of pelvic floor pathology may enable personalized treatment planning and accurate outcome predictions.

Various treatment options are available for pelvic floor symptoms resulted from these conditions; those include hormonal treatment, topical lubricants, physiotherapy, insertion of vaginal pessaries and tampons, and various types of surgical procedures. New minimally invasive procedures based on light and radio waves are available that are aimed at vaginal tissue rejuvenation; these include thermal energy deposition in the vaginal tissue using $CO_2$ laser, Er:YAG laser, combinations of diode lasers at various wave lengths, and radio frequency (RF). Despite the technology advancements, publications describing such tissue changes are based on patient's satisfaction scales and doctor's evaluation measures; however, only a few studies include histological documentation comparing tissue changes before and after treatment. Several external genital disorders such a Lichen Sclerosus and Vestibulitis (Vesibulodynia) are causing impact on women's quality of life and no curative treatment is available. Non-invasive imaging modalities described herein will monitor medical treatments and energy-based therapeutics in the same modality as the intravaginal, intraurethral, and urinary bladder.

The present invention may allow for non-invasive information about the vaginal histology to be obtained, which include: non-keratinized stratified squamous epithelium, the lamina propria (leukocytes, fibroblasts, collagen and blood vessels), the muscular layer, inner—circular, and outer—longitudinal of smooth muscle, as well as the inner layer, the adventitia, bordering the muscularis, which is fairly dense and contains many elastic fibers. Loose connective tissue with a prominent venous plexus forms the outer part of the adventitia. In addition, the present invention may also provide information on tissue microvasculature, blood flow, and thermal damage.

SUMMARY OF THE INVENTION

In some aspects, the present invention features an Optical Coherence Tomography (OCT) probe designed to perform non-invasive real-time monitoring of micron level changes in the vaginal epithelium, lamina propria, muscularis and adventitia, depending on technology specifications and tissue dimensions. Real time, in-vivo characterization of these layers prior to any treatment (medical, hormonal, physiotherapy) and especially the newly developing minimally invasive deposition of thermal energy, may offer information for patient selection and technology preference for early stage pelvic floor conditions. Such information may also contribute to the understanding of vaginal lubrication and urinary incontinence (stress—SUI, or mixed cause of incontinence—MUI).

In addition to the vaginal OCT probe, this invention also includes integration into laser and energy-based therapeutic device for intraoperative imaging. Besides OCT, other imaging modality such as ultrasound, fluorescence, and photoacoustic imaging can be simultaneously acquired to retrieve functional information and more accurate diagnosis. None of the presently known prior references or work has the unique inventive technical feature of the present invention.

According to some aspects, the present invention features a device for the simultaneous treatment and monitoring of pelvic floor disorders, combining optical tomography and energy based therapeutic treatment into a combined probe. In one embodiment, the device may comprise a treatment device capable of emitting a treatment beam, an imaging probe disposed on a side of the treatment device and capable of detecting an interference signal, a disposable, optically clear tube cover enclosing the treatment device and the imaging probe, a swept source laser or broad band light source capable of generating light for performing optical coherence tomography (OCT), a photo detector used to detect the interference signal, a fiber optic circulator optically connected to the swept source laser or broad band light source, and to the photo detector, and to the optical fiber of the imaging probe, capable of acting as a non-reciprocating one-directional three-port device to sequentially direct light from the swept source laser or broad band light source to the imaging probe and direct a reflected interference signal from the imaging probe to the photo detector, a motor control board used to drive the micro-motor of the imaging probe, and a data acquisition board operatively connected to a communication port of the swept source laser or broad band light source and the photo detector, capable of receiving a timing signal from the laser or broad band light source and recording the interference signal at the beginning of every sweep cycle.

In one embodiment, the treatment beam may comprise a first glass tube for housing the treatment device, a mirror disposed the distal end of the first glass tube so as to reflect light directed from the proximal end of the tube outward through the tube, a treatment laser disposed within the proximal end of the first glass tube, a pixel beam splitter disposed within the tube so as to be in a light pathway of the treatment laser, and at least one lens disposed between the pixel beam splitter and the mirror so as to focus light from the pixel beam splitter into the mirror. The treatment laser emits a light beam which is directed into the pixel beam splitter. The pixel beams are directed into the lens and focused on the mirror, which reflects the beams out of the tube. In another embodiment, the imaging probe may comprise a second glass tube for housing the imaging probe, a micro-motor disposed within a distal end of the second glass tube and controlled by a motor driver, a rod mirror mounted on the motor, an optical fiber disposed within a proximal end of the second glass tube and oriented so as to direct light into a focusing lens that is disposed so as to direct laser light from the optical fiber into the rod mirror, and a metal housing. In some embodiments, the fiber optic circulator directs light from the swept source laser or broad band light source into the imaging probe. The light is transmitted through the focusing lens to the rod mirror, and out into the tissue. The micro-motor rotates the rod mirror to direct the light. After passing through tissue, light is reflected back into the rod mirror and directed into the optical fiber. The fiber optic circulator directs the light into the photo detector, which receives the light and transmits a signal to the data acquisition board, which records the signal.

According to another embodiment, the device may comprise a treatment device, capable of emitting a treatment beam, an imaging probe disposed on a side of the treatment device and capable of detecting an interference signal, a disposable, optically clear tube cover enclosing the treatment device and imaging probe, a micro-motor centrally disposed within the distal end of the tube cover, a second rod mirror mounted on the micro-motor, wherein the second reference mirror is disposed so as to reflect light from the first rod mirror which has been reflected off of the back side of the double-sided mirror of the treatment device, a swept source laser or a broad band light source capable of generating light for performing optical coherence tomography (OCT), a photo detector used to detect the interference signal, a fiber optic circulator optically connected to the swept source laser or broad band light source, and to the photo detector, and to the optical fiber of the imaging probe, capable of acting as a non-reciprocating one-directional three-port device to direct light from the swept source laser or broad band light source to the imaging probe and sequentially direct a reflected interference signal from the imaging probe to the photo detector, a motor control board used to drive the micro-motor, and a data acquisition board used to record the interference signal.

In some embodiments, the treatment device may comprise a first glass tube for housing the treatment device, a double-sided mirror disposed at the distal end of the first glass tube, a treatment laser disposed within the proximal end of the first glass tube, a pixel beam splitter disposed within the tube so as to be in a light pathway of the treatment laser, and at least one lens disposed so as to focus light from the pixel beam splitter into a front side of the mirror. The treatment laser of the treatment device emits light, which is directed into the beam splitter and through at least one lens. The light is directed into the mirror and transmitted into the surrounding tissue. In other embodiments, the imaging probe may comprise a second glass tube for housing the imaging probe, an optical fiber disposed within the proximal end of the tube, a first rod mirror disposed on the distal end of the second glass tube so as to direct light from the swept source laser or broadband light source into a back side of the double-sided mirror of the treatment device, and a metal housing. The fiber optic circulator directs light from the swept source laser or broad band light source into the imaging probe. The light is transmitted through the focusing lens to the first rod mirror, reflected onto the mirror of the treatment device, and then reflected onto the second rod mirror and out into the tissue. The micro-motor rotates the second rod mirror to direct the light, and after passing through tissue, light is reflected back into the mirror. The light is directed into the optical fiber and the fiber optic circulator directs the light into the photo detector, which receives the light and transmits a signal to the data acquisition board, which records the signal.

In yet other embodiments, the device may comprise a glass tube, a treatment laser, a swept source laser or broad band light source capable of generating the light for performing optical coherence tomography (OCT), a collimator configured to focus light from the swept source laser or broad band light source into a parallel beam, a pixel beam splitter disposed in the path of the treatment laser light and configured to create laser pixel beams, a dichroic mirror disposed in the path of the treatment laser light and OCT light and capable of combining the treatment beam and the diagnostic beam into a single combined beam, at least one galvanometer-mounted mirror disposed so as to reflect the parallel beam from the collimator onto the dichroic mirror, a first lens disposed in the path of the laser light between the beam splitter and dichroic mirror and configured to focus laser light on the dichroic mirror, a second lens disposed in the path of the collimator configured to direct the parallel beam onto the at least one galvanometer-mounted mirror, a relay lens disposed to focus light reflected from the dichroic mirror into the glass tube lengthwise, a focusing lens disposed so as to direct the combined beam from the dichroic mirror into a directive mirror disposed to reflect light from the focusing lens into the surrounding tissue, a disposable, optically clear tube cover enclosing the probe, a photo detector capable of detecting an interference signal, a fiber optic circulator optically connected to the swept source laser or broad band light source, and to the photo detector, and to an optical fiber of an imaging probe, capable of acting as a non-reciprocating one-directional three-port device to sequentially direct light from the swept source laser or broad band light source to the imaging probe and direct a reflected interference signal from the imaging probe to the photo detector, a motor control board used to drive the galvanometer-mounted mirror, and a data acquisition board used to record the interference signal.

In some embodiments, the fiber optic circulator directs light from the swept source laser or broad band light source into the collimator. The light is transmitted through the second lens to the at least one galvanometer-mounted mirror, which is rotated to move the beam of the swept source laser or broad band light source. The beam movement produces two dimensional scanning. The light is reflected onto the dichroic mirror, and the laser beam from the laser is split by the pixel beam splitter into laser pixel beams. The first lens focuses the laser light onto the dichroic mirror, and the dichroic mirror combines the laser beam and the beam from the swept source laser or broad band light source into the combined beam. The relay lens focuses the combined beam onto the focusing lens, which focuses the light onto the directive mirror, which reflects light into the surrounding tissue. After passing through tissue, light is reflected back into the directive mirror, and directed into the collimator following the same path as emission of OCT light. The light travels through the optical fiber, and the fiber optic circulator directs the light into the photo detector. The photo detector receives the light and transmits a signal to the data acquisition board, which records the signal. The treatment laser emits light, which is directed into the beam splitter, through at least one lens, into the directive mirror and transmitted into the surrounding tissue.

According to some other embodiments, the device may comprise an imaging probe capable of detecting an interference signal, a disposable, optically clear cover enclosing the probe, at least one array of electrodes disposed on an outer surface of the disposable cover and capable of emitting radio frequency (RF) energy at a frequency useful for treatment, a photo detector used to detect the interference signal, a fiber optic circulator optically connected to the swept source laser or broad band light source, and to the photo detector, and to the optical fiber of the imaging probe, capable of acting as a non-reciprocating one-directional three-port device to direct light from the swept source laser or broad band light source to the imaging probe, and sequentially direct a reflected interference signal from the imaging probe to the photo detector, a motor control board used to drive the micro-motor, and a data acquisition board used to record the interference signal. In one embodiment, the imaging probe may comprise a glass tube acting as a housing for the imaging probe, a swept source laser or a broad band light source capable of generating light for performing optical coherence tomography (OCT), a micro-motor disposed within a distal end of the glass tube, a rod mirror mounted on the motor, an optical fiber disposed within a proximal end of the tube, operatively connected to a photo detector and the swept source laser or broad band light source, a focusing lens disposed so as to direct laser light from the optical fiber into the rod mirror, and a metal housing.

In some embodiments, the fiber optic circulator directs light from the swept source laser or broad band light source into the optical fiber. The light is transmitted through the focusing lens to the rod mirror, and out into the tissue. The micro-motor rotates the mirror to direct the light. After passing through tissue, light is reflected back into the mirror and directed into the optical fiber. The fiber optic circulator directs the light into the photo detector, which receives the light and transmits a signal to the data acquisition board, which records the signal. The electrodes are charged with an oscillating voltage, controlled by a function generator and amplifier, to generate RF energy waves at the frequency useful for treatment, which are emitted into the surrounding tissue.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

DESCRIPTION OF PREFERRED EMBODIMENTS

Figure 1A:
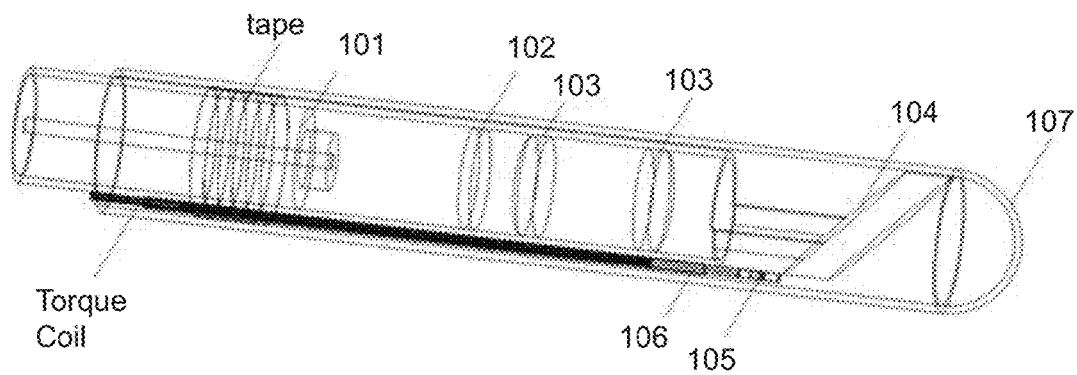
FIG. 1A shows an exemplary schematic view of an integrated probe.

Following is a list of elements corresponding to a particular element referred to herein:

- 101, 301 treatment laser
- 102, 302 pixel beam splitter
- 103, 202, 309 lens
- 104, 204, 304 mirror
- 106, 206, 405 metal housing
- 107, 207, 410 tube cover
- 108, 208, 403 optical fiber
- 109, 404 focusing lens
- 110, 210, 215, 402 rod mirror
- 111, 211, 401 micro-motor
- 113, 213 treatment beam
- 105 imaging probe
- 112 second glass tube
- 305 relay lens
- 306 focusing lens
- 307 directive mirror
- 308 collimator
- 310 galvanometer-mounted mirror
- 420 array of electrodes
- 501 support material
- 502 washer
- 503 bearing
- 504 inflatable balloon
- 505 expansion valve
- 701 gradient-index (GRIN) optics lens
- 703 galvanometer-actuated mirror
- 706 2D MEMS mirror
- 707 piezoactuator
- 801 ultrasound (US) pulse transducer
- 1001 swept source laser or broad band light source
- 1003 fiber optic circulator As known to one of ordinary skill in the art, the female genital tract may be significantly affected by normal and traumatic vaginal deliveries, and by hormonal changes related to cessation of ovarian function during the transition from the reproductive to post-menopausal age. Technical parameters of energy-based devices, vis-a-vis the physiologic characteristics of the target tissue, may influence possible cell activation for tissue restoration. In the case of vaginal mucosa in which epithelial cells and the ground substance of the connective tissue are rich in water, it is important to consider that healthy premenopausal mucosa is highly hydrated, differing from the atrophic postmenopausal mucosa where the main characteristic is the dryness. As such, a controlled power of the source has to be used. Based on successful treatments of aging-related modifications affecting the skin by using fractional laser, the technology was adapted to the vaginal mucosa.

The related histological modifications of postmenopausal atrophic vaginal mucosa following fractional $CO_2$ laser, Er:YAG laser and RF treatments has been reported as the structural basis for the understanding of the fine mechanisms responsible of the clinical health restoration. However, in view of the ethical limitation to justify tissue biopsies, the information about histological changes and the sequence of events that lead to vaginal tissue rejuvenation is limited.

Epithelial cells are distributed in many layers: a basal layer, firmly attached to the basal lamina interfacing the connective tissue and supporting a dynamic cell turnover to the whole epithelium, para-basal and intermediate layers, and a superficial layer where the most superficial cells are shedding into the vaginal lumen. This is representative of a sort of secretory activity, which is important considering that vaginal mucosa is devoid of glands, and the secretory activity responsible of vaginal health is closely related to the shedding of the most superficial cells in the epithelium. Starting from the basal layer, where epithelial cells are proliferating in order to substitute under the control of a dynamic mechanism, the loss of shedding cells at the mucosal surface, epithelial cells are undergoing a process of differentiation synthesizing glycogen. Glycogen begins to be synthesized in cells of the intermediate layers, and it is subsequently stored in the superficial cells. When the most superficial cells are shed in the vaginal lumen, their content of glycogen is delivered free at the epithelial surface, favoring the activity of Lactobacilli, which is the main factor in keeping the low healthy pH of the vaginal inner environment.

The pre-menopausal lamina propria is rich in blood vessels, penetrating as small capillaries inside papillae, providing metabolic support (nutrients, oxygen and other molecules) to the intermediate and superficial layers of cells. Collagen fibers are organized in compact bundles differently oriented, and together with elastic fibers, constituting an effective support to the mucosal part of the vaginal wall. During menopause, the decline and arrest of ovarian estrogen production is related to significant structural and functional changes in the vaginal mucosa, resulting in atrophy. In post-menopause, vaginal mucosa atrophy is characterized by a significant thinning of the epithelium, which is constituted by several layers of small cells, with a reduction of epithelial renewal dynamics and the related absence of superficial cells desquamation. The epithelium-connective tissue interface appears smooth due to the reduction and/or absence of papillae and blood vessels.

After fractional laser treatment of post-menopausal mucosa, the squamous stratified epithelium appeared thick, formed by 20-40 cell layers providing cells to upper layers for differentiation (in the intermediate layers) and superficial shedding. Basal layer cells appeared closely packed as in any continuously renewing stratified epithelium. The intermediate layer cells appeared enlarged, with the nucleus surrounded by a wide cytoplasm. Epithelial renewal, and the renewed synthesis, storage and delivery of glycogen, is realistically the consequence of the stimulation of the connective tissue to restore its structure and functionality, with a renewal of the matrix, not only the fibrillar components, but also the highly hydrophilic molecular components of the ground matrix. In this way, the high hydration and permeability of the extracellular matrix is improved, permitting a high rate of molecular traffic both inside the connective tissue and between the vessels and the epithelium (which is not vascularized), stimulating also the epithelium to restore the lost functions.

Microscopic findings obtained from few biopsies before and following fractional $CO_2$ laser treatment demonstrate the recovery of the whole mucosal structures supporting a full functional restored physiological condition both in the epithelial and connective tissue compartments. Observed modifications of the mucosal structures following fractional $CO_2$ treatment can be summarized as follows.

The epithelium appears thick, without signs of atrophy. It is formed by many cell layers, with a basal layer of closely packed proliferating cells giving rise to big intermediate and superficial cells. A highly significant storage of glycogen is present in the large epithelial cells forming the intermediate and superficial layers, expression of a restored differentiative mechanism oriented to the synthesis of glycogen. A high degree of epithelial exfoliation with superficial cells filled with glycogen shedding at the epithelial surface is observable. This is important because, as in the premenopausal mucosa, the lactic acid produced by *Lactobacilli vaginalis* (bacteria physiologically resident in the vagina) fed by glucose from glycogen, acidifies the vaginal transudate fluid at the mucosal surface, restoring an inner healthy acid vaginal environment, while preventing of the colonization of yeasts and other bacterial pathogens.

In the connective tissue (termed lamina propria), fibroblasts are characterized by a rich content of organelles, as an extended rough endoplasmic reticulum which is the site of synthesis of procollagen molecules, with cisternae often dilated. A rich content of blood vessels in the connective tissue supporting a renewed activity of fibroblasts and capillaries penetrating the newly-formed papillae underneath the epithelium for a better metabolic support also of epithelial cells proliferation and differentiation.

A relevant aspect that has to be underlined on the modifications of atrophic vaginal mucosa following fractioned laser treatment is the restoration of a physiological acid pH in the vaginal inner environment, which is the consequence of the restored dynamics in the epithelium (cell turnover) at the same time as the restoration of differentiative mechanisms leading to the delivery of glycogen. Glycogen delivered at the vaginal epithelial surface is hydrolyzed to glucose, feeding Lactobacilli which produce lactic acid and consequently lower pH to a correct acidic condition which characterize the inner healthy environment of vagina with relief from adverse symptoms.

Fractioned laser and other energy based therapies of atrophic vaginal mucosa leads to new production of collagen and ground substance components within the connective tissue, and glycogen and acidic mucins within the epithelium and on the epithelial surface, are rebalancing and restoring vaginal mucosa from atrophy induced by the absence of ovarian estrogens, resulting in a highly significant improvement in clinical symptoms.

Most treatment protocols include 2-3 treatment sessions, 2-3 consecutive tissue exposure, at 4-6 weeks intervals, and are not based on highly scientific data. Monitoring of patient's satisfaction is based on previously published questionnaires, as well as care givers' subjective impression and visual scales and scores. No consecutive histologic observations are available to justify these treatment protocols, and the availability of sham controls is limited. Moreover, the duration of tissue changes following energy based therapy is not known, and recommendations to perform touch-up therapy at 6-12 months are not supported by objective parameters.

The proposed technology of the present invention provides a new standard of non-invasive optical tissue monitoring in order to define pre- and post-menopausal parameters, pre- and post-treatment microscopic changes, and offers an objective scientific tool in order to compare currently available energy based devices and treatment protocols.

Figure 1B:
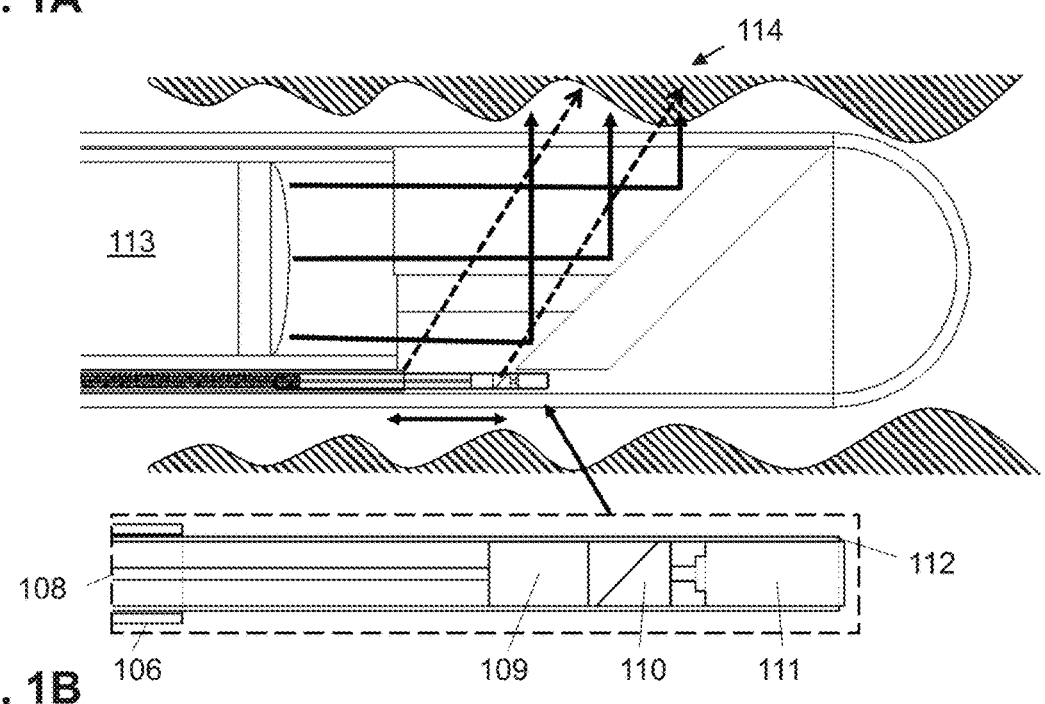
FIG. 1B shows an enlarged schematic view of the probe scanning a vaginal wall.
Figure 2:
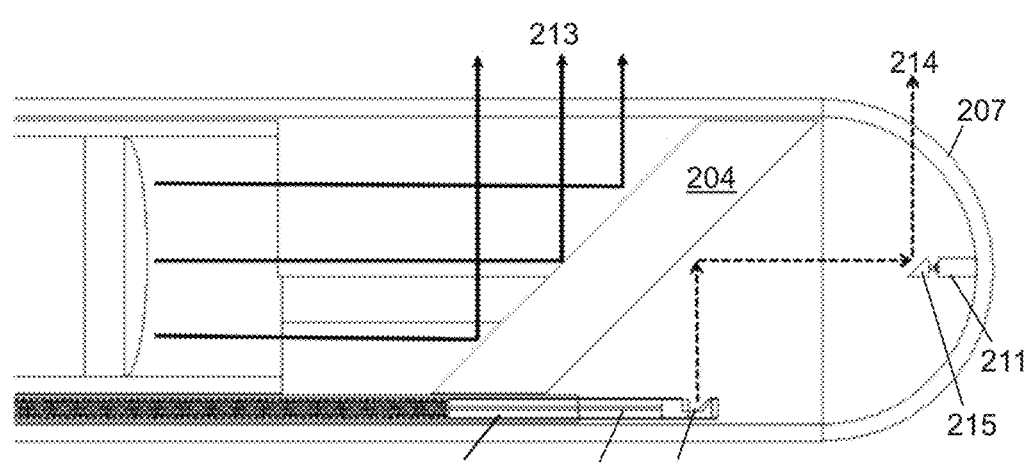
FIG. 2 shows a non-limiting embodiment of an integrated coaxial probe for simultaneous treatment and diagnosis of a vulvovaginal wall.

Referring now to FIGS. 1A-23, in some embodiments, the present invention features an apparatus for monitoring an inner surface of vaginal wall as well as vulva surface during the treatment. In some embodiments, an imaging probe may be placed next to a laser ablation device, as shown in FIGS. 1A-1B. The entire device may be protected by a disposable optically-clear tube. A light source and sensor for the imaging probe are placed external to the tube housing and connected to the probe via optical fibers. In the imaging probe, a reflective mirror and a micro-motor may be placed at a distal end to acquire cross-sectional images. In addition, the probe can be moved back and forth to scan volumetric information. In some embodiments, an OCT light is reflected at the double-side mirror and micro-motor to create co-axial scanning (FIG. 2). Other imaging probe schemes can be utilized, such as an external rotational probe, a fiberoptic probe, and a linear scan probe.

According to some embodiments, the present invention features a device for simultaneous treatment and monitoring of pelvic floor disorders. The device may combine optical tomography and energy based therapeutic treatment. In some embodiments, the device may comprise a swept source laser or broad band light source, used to generate the light for performing optical coherence tomography (OCT), operatively connected to a combined probe capable of transmitting therapeutic energy and OCT light, and receiving OCT signals. In some embodiments, the device may further comprise a photo detector used to detect the interference signal, and a data acquisition board used to record the interference signal.

In some embodiments, the combined probe may comprise a treatment device capable of emitting a treatment beam (113), an imaging probe (105) disposed on a side of the treatment device and capable of detecting the interference signal, and a disposable, optically clear tube cover (107) enclosing the treatment device and the imaging probe (105). In one embodiment, the treatment device may comprise a first glass tube acting as a housing for the treatment device, a mirror (104) disposed the distal end of the first glass tube, a treatment laser (101) disposed within the proximal end of the first glass tube, a pixel beam splitter (102) disposed within the tube so as to be in a light pathway of the treatment laser, and at least one lens (103) disposed so as to direct light from the treatment laser into the mirror (104). In another embodiment, the imaging probe (105) may comprise a second glass tube (112) acting as a housing for the imaging probe, a micro-motor (111) disposed within a distal end of the second glass tube and controlled by a motor driver, a rod mirror (110) mounted on the motor, an optical fiber (108) disposed within a proximal end of the second glass tube and operatively connected to the photo detector, a focusing lens (109) disposed so as to direct laser light from the mirror into the optical fiber (108), and a metal housing (106).

In other embodiments, the device may comprise a fiber optic circulator (1003), optically connected to the swept source laser or broad band light source, and to the photo detector, and to the optical fiber of the imaging probe. The fiber optic circulator can act as a non-reciprocating one-directional three-port device to sequentially direct light from the swept source laser or broad band light source (1001) to the imaging probe, and direct a reflected interference signal from the imaging probe to the photo detector. The device may further comprise a motor control board used to drive the micro-motor of the imaging probe, and a data acquisition board operatively connected to a communication port of the swept source laser or broad band light source and the photo detector. The data acquisition board may receive a timing signal from the laser or broad band light source and recording the interference signal at the beginning of every sweep cycle.

When the device is used, the fiber optic circulator directs light from the swept source laser or broad band light source into the imaging probe (105), and the light is transmitted through the focusing lens (109) to the rod mirror (110), and out into the tissue. The micro-motor (111) rotates the rod mirror (110) to direct the light, and after passing through tissue, light is reflected back into the rod mirror (110) and directed into the optical fiber (108). The fiber optic circulator directs the light into the photo detector, which receives the light and transmits a signal to the data acquisition board, which records the signal. In another embodiment, the treatment laser (101) emits light, which is directed into the beam splitter (102) and through at least one lens (103). The light is then directed into the mirror (104) and transmitted into the surrounding tissue.

According to other embodiments, the device may comprise the swept source laser or a broad band light source used to generate the light for performing optical coherence tomography (OCT) and operatively connected to a combined probe, the combined probe capable of transmitting therapeutic energy and OCT light, receiving OCT signals, and co-axial scanning, the photo detector used to detect the interference signal, and the data acquisition board used to record the interference signal. In some embodiments, the combined probe comprises the treatment device capable of emitting a treatment beam (213), the imaging probe disposed on a side of the treatment device and capable of detecting the interference signal, a disposable, optically clear tube cover (207) enclosing the treatment device and imaging probe, a micro-motor (211) centrally disposed within the distal end of the tube cover (207), and a second rod mirror (215) mounted on the motor and disposed so as to reflect light from the first rod mirror.

In some embodiments, the treatment device may comprise a first glass tube acting as a housing for the treatment device, a mirror (204) disposed at the distal end of the first glass tube, a treatment laser disposed within the proximal end of the first glass tube, a pixel beam splitter disposed within the tube so as to be in a light pathway of the treatment laser, and at least one lens disposed so as to direct laser light into the mirror. In some embodiments, the imaging probe may comprise a second glass tube, acting as a housing for the imaging probe, a first rod mirror (210), an optical fiber (208) disposed within the proximal end of the tube and operatively connected to a photo detector, a focusing lens disposed so as to direct laser light from the mirror into the optical fiber, and a metal housing (206).

In other embodiments, the device may comprise a fiber optic circulator (1003), optically connected to the swept source laser or broad band light source, and to the photo detector, and to the optical fiber of the imaging probe. The fiber optic circulator can act as a non-reciprocating one-directional three-port device and sequentially direct a reflected interference signal from the imaging probe to the photo detector. The device may further comprise a motor control board used to drive the micro-motor, and a data acquisition board used to record the interference signal.

When the device is used, the fiber optic circulator directs light from the swept source laser or broad band light source into the imaging probe. The light is transmitted through the focusing lens to the first rod mirror (210), reflected onto the mirror of the treatment device (204), and reflected onto the second rod mirror (215), and out into the tissue. The micro-motor (211) rotates the second rod mirror (215) to direct the light, and after passing through tissue, the light is reflected back into the mirror. The light is directed into the optical fiber (208), and the fiber optic circulator directs the light into the photo detector. The photo detector receives the light and transmits a signal to the data acquisition board, which records the signal. In some other embodiments, the treatment laser of the treatment device emits light, which is directed into the beam splitter and through at least one lens. The light is directed into the mirror (204) and transmitted into the surrounding tissue.

Figure 3A:
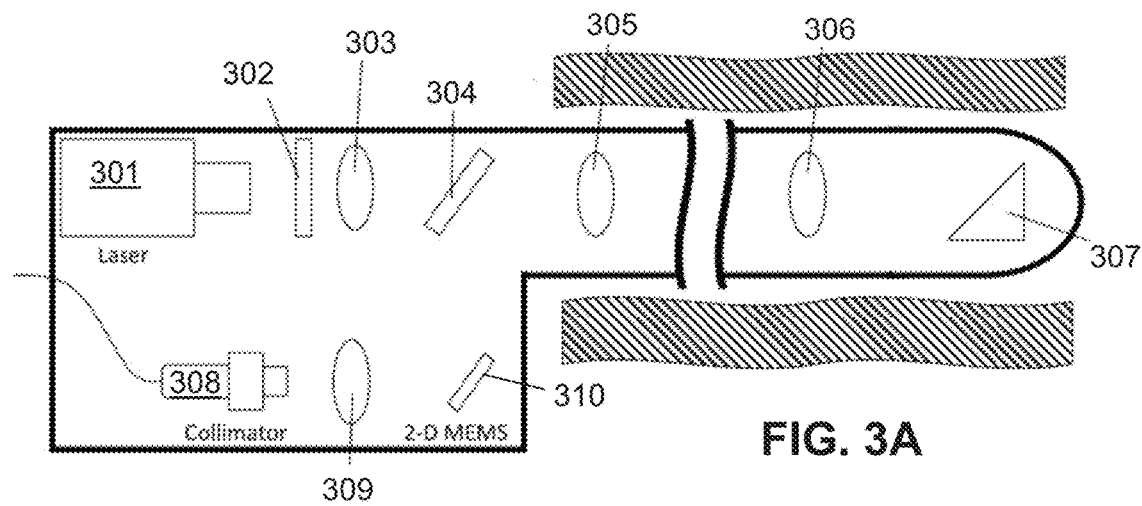
FIG. 3A shows a non-limiting embodiment of a co-axial probe using 2-D MEMS scanning.
Figure 3B:
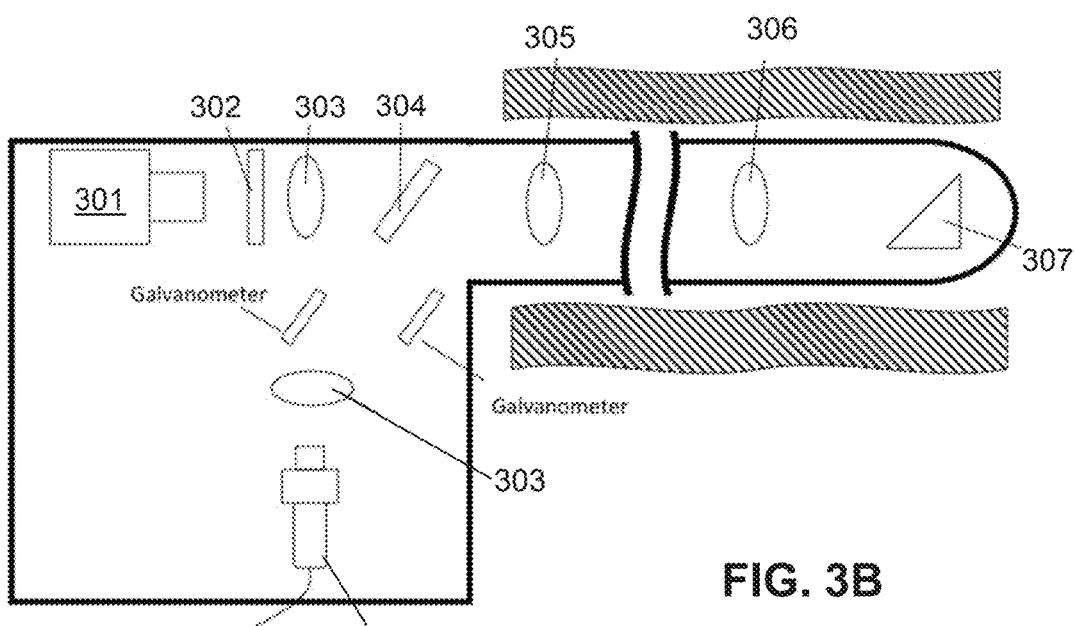
FIG. 3B shows a non-limiting embodiment of a co-axial probe using 2-axis galvanometer scanning.

According to other embodiments, an OCT beam may be coupled to the laser ablation device, as shown in FIGS. 3A-3B. Dichroic mirror combines OCT light with laser light and focus at the vaginal surface. 2D MEMS mirror or two galvanometers may be utilized to acquire 2-dimensional scanning of OCT beam. In one embodiment, the device for the simultaneous treatment and monitoring of pelvic floor disorders, combining optical tomography and energy based therapeutic treatment may comprise a swept source laser or a broad band light source used to generate the light for performing optical coherence tomography (OCT), and operatively connected to a combined probe capable of transmitting therapeutic energy and OCT light, and receiving OCT signals, a photo detector used to detect an interference signal, and a data acquisition board used to record the interference signal.

In some embodiments, the combined probe may comprise a glass tube, a treatment laser (301) acting as an energy source for the probe, a collimator (308) configured to focus light from the swept source laser or broad band light source into a parallel beam, a pixel beam splitter (302) disposed in the path of the laser light and configured to create laser pixel beams, and a disposable, optically clear tube cover enclosing the probe. In other embodiments, the combined probe may further comprise a dichroic mirror (304) disposed in the path of the laser light capable of combining the parallel beam and the laser light into a single combined beam, and at least one galvanometer-mounted mirror (310) controlled by an electronic driver and disposed so as to reflect the parallel beam from the collimator onto the dichroic mirror. A motor control board may be used to drive the galvanometer-mounted mirror. In other embodiments, the combined probe may further comprise a first lens (303) disposed in the path of the laser light, after the beam splitter, and configured to focus laser light on the dichroic mirror, a second lens (309) disposed in the path of the collimator configured to direct the parallel beam onto the at least one galvanometer-mounted mirror, a relay lens (305) disposed to focus light reflected from the dichroic mirror into the glass tube lengthwise, a focusing lens (306) disposed so as to direct the combined beam from the dichroic mirror into a directive mirror, and the directive mirror (307) disposed to reflect light from the focusing lens into the surrounding tissue.

In further embodiments, the device may include a fiber optic circulator (1003), optically connected to the swept source laser or broad band light source, and to the photo detector, and to an optical fiber of an imaging probe. The fiber optic circulator can act as a non-reciprocating one-directional three-port device to sequentially direct light from the swept source laser or broad band light source (1001) to the imaging probe, and direct a reflected interference signal from the imaging probe to the photo detector.

When this embodiment of the device is used, the fiber optic circulator directs light from the swept source laser or broad band light source into the collimator (308), and the light is transmitted through the second lens (309) to the at least one galvanometer-mounted mirror (310). The galvanometer-mounted mirror is rotated to move the beam of the swept source laser or broad band light source, which produces two-dimensional scanning. The light is reflected onto the dichroic mirror (304). The laser beam from the laser (301) is split by the pixel beam splitter (302) into laser pixel beams. The first lens (303) focuses the laser light onto the dichroic mirror (304), which combines the laser beam and the beam from the swept source laser or broad band light source into the combined beam. The relay lens (305) focuses the combined beam onto the focusing lens (306), which focuses the light onto the directive mirror (307), which reflects light into the surrounding tissue. After passing through tissue, light is reflected back into the directive mirror. The light is directed into the collimator following the same path as emission of OCT light. Light travels through the optical fiber, and the photo detector receives the light and transmits a signal to the data acquisition board, which records the signal. In further embodiments, the treatment laser emits light, which is directed into the beam splitter and through at least one lens. The light is then directed into the directive mirror and transmitted into the surrounding tissue.

Figure 4A:
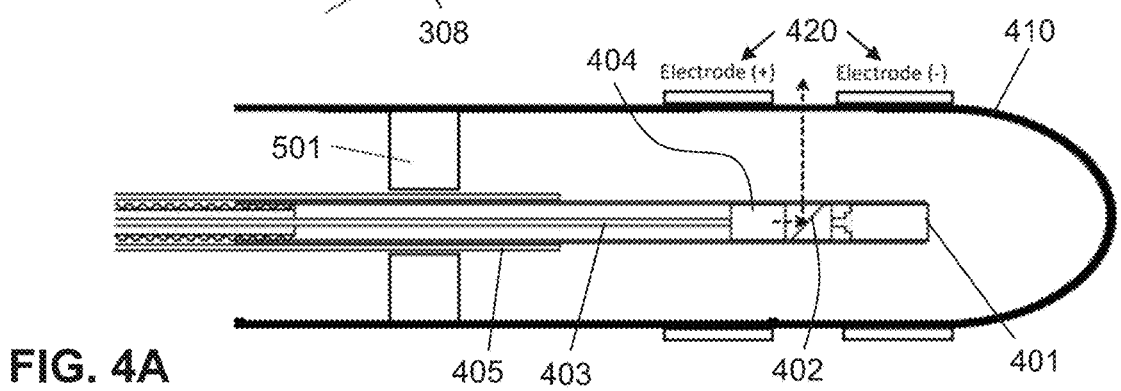
FIG. 4A shows a non-limiting embodiment of an OCT radio frequency (RF) probe with bearing. Electrodes are attached to the surface of protective tube.
Figure 4B:
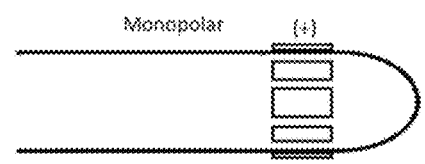
FIG. 4B shows the OCT RF probe configured for monopolar RF treatment.
Figure 4C:
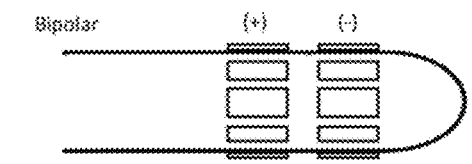
FIG. 4C shows the OCT RF probe configured for bipolar RF treatment

In some embodiments, an imaging probe may be placed inside a rigid disposable tube that has electrodes on the surface for radio frequency therapy (FIGS. 4A-4C). The OCT probe is placed in the center of the tube for coaxial scanning. Referring to FIG. 4B, a single array of electrodes can provide monopolar radio frequency treatment. Referring to FIG. 4C, two arrays of positive and negative electrodes can provide bipolar frequency treatment. Different OCT probes can be utilized. In one embodiment, a bearing may hold the external rotational probe and provide stable and high-speed rotational OCT imaging. In another embodiment, a supporting material can hold a micro-motor probe. Other probes include fiberoptic probe and linear scanning probe.

According to some embodiments, the device may comprise a swept source laser or a broad band light source used to generate the light for performing optical coherence tomography (OCT) and operatively connected to a combined probe capable of transmitting therapeutic energy and OCT light, and receiving OCT signals, a photo detector used to detect an interference signal, and a data acquisition board used to record the interference signal. In some embodiments, the combined probe may comprise an imaging probe capable of detecting an interference signal comprising a glass tube acting as a housing for the imaging probe, a micro-motor (401) disposed within a distal end of the glass tube, a motor control board used to drive the micro-motor, a rod mirror (402) mounted on the motor, an optical fiber (403) disposed within a proximal end of the tube and operatively connected to the photo detector, a focusing lens (404) disposed so as to direct laser light from the rod mirror into the optical fiber, and a metal housing (405). In other embodiments, the combined probe may have a disposable, optically clear cover (410) enclosing the glass tube. In some other embodiments, the combined probe may comprise at least one array of electrodes (420) disposed on an outer surface of the disposable cover, capable of emitting radio frequency (RF) energy at a frequency useful for treatment. In further embodiments, the device may comprise a fiber optic circulator (1003), optically connected to the swept source laser or broad band light source, and to the photo detector, and to the optical fiber of the imaging probe. The fiber optic circulator acts as a non-reciprocating one-directional three-port device to direct light from the swept source laser or broad band light source (1001) to the imaging probe, and sequentially direct a reflected interference signal from the imaging probe to the photo detector.

When this embodiment of the device is used, the fiber optic circulator directs light from the swept source laser or broad band light source into the optical fiber (403). The light is transmitted through the focusing lens (404) to the rod mirror (402), and out into the tissue. The micro-motor (401) rotates the mirror to direct the light. After passing through tissue, light is reflected back into the mirror, and directed into the optical fiber (403). The fiber optic circulator directs the light into the photo detector and the photo detector receives the light and transmits a signal to the data acquisition board, which records the signal. In some embodiments, the electrodes are charged with an oscillating voltage, controlled by a function generator and amplifier, to generate RF energy waves at the frequency useful for treatment, which are emitted into the surrounding tissue.

Figure 5A:
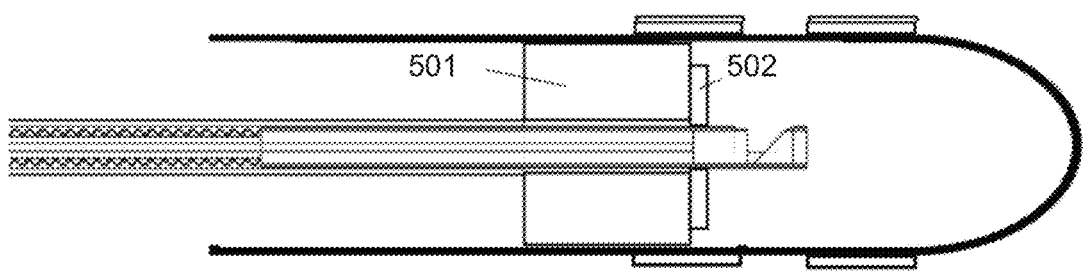
FIG. 5A shows a non-limiting embodiment of an OCT RF probe with washer.
Figure 5B:
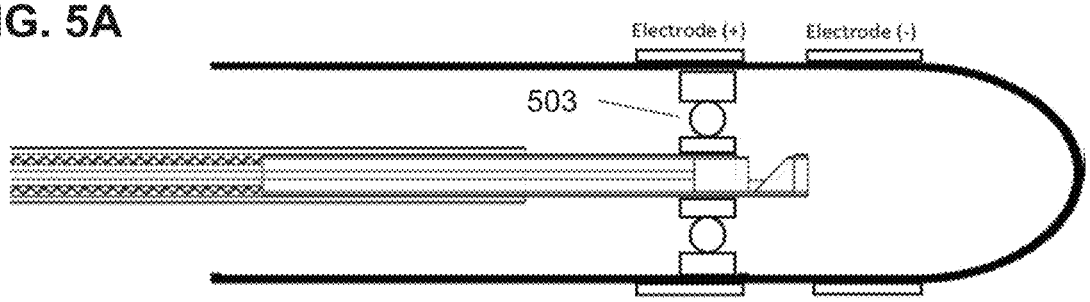
FIG. 5B shows a non-limiting embodiment of an OCT RF probe with a bearing.
Figure 5C:
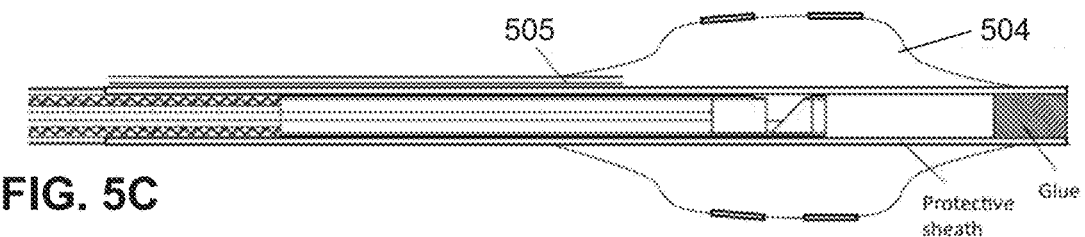
FIG. 5C shows a non-limiting embodiment of an OCT RF probe with an inflatable balloon.

In some embodiments, the probe may further comprise a support material (501) that holds the imaging probe in a center of the cover when the imaging probe rotates within the cover. In one embodiment, as shown in FIG. 5A, a washer may be attached to the rotational probe and rotate with the probe in front of a support material to provide stable and high-speed rotation for an RF/OCT integrated probe. In one embodiment, the washer (502) holds the imaging probe in a center of the cover when the imaging probe rotates within the cover. In another embodiment, as shown in FIG. 5B, a bearing may be attached to the rotational probe. The bearing (503) holds the imaging probe in a center of the cover when the imaging probe rotates within the cover. In yet another embodiment, as shown in FIG. 5O, an imaging probe may be placed inside an inflatable balloon that has electrodes on the surface for radio frequency therapy. In some embodiments, the cover may be an inflatable balloon (504) and an expansion valve (505) is coupled to the cover for supplying air to inflate the balloon during treatment. In other embodiments, the cover may be a rigid, optically clear tube.

Figure 6A:
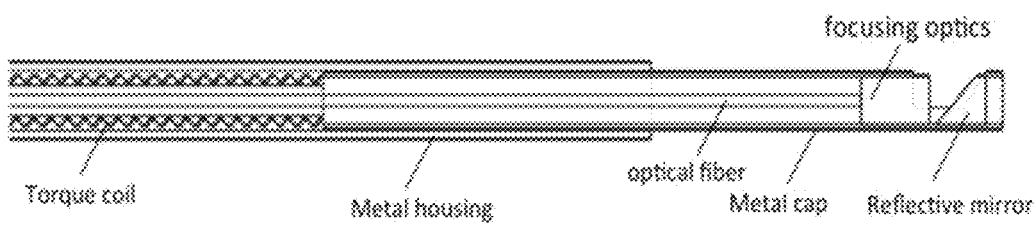
FIG. 6A shows a non-limiting embodiment of an external rotating probe.
Figure 6B:
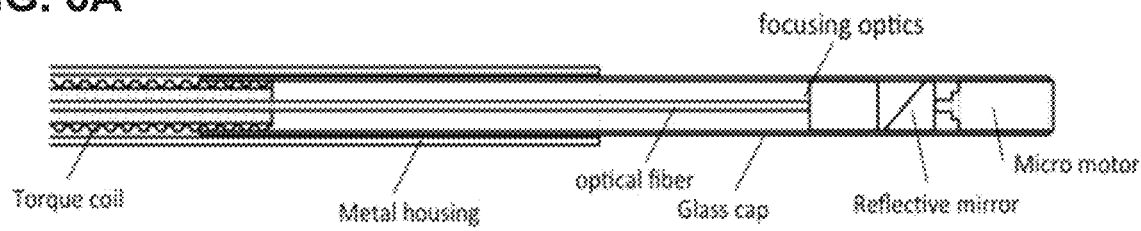
FIG. 6B shows a non-limiting embodiment of a micro-motor probe.
Figure 6C:
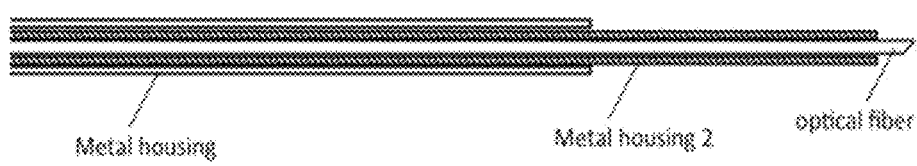
FIG. 6C shows a non-limiting embodiment of a fiberoptic probe.

For any integrated OCT/laser or OCT/RF devices that has an OCT probe attached, various designs of OCT probes can be incorporated. In one embodiment, as shown in FIGS. 6A-6O, a rotational imaging scheme can be utilized. For example, the imaging probe may be rotated by an external mechanism. In one rotational probe design, an external motor can rotate the entire OCT probe inside a metal housing (FIG. 6A). In another rotational probe design, a micro-motor may be placed at the distal end for internal rotation (FIG. 6B). In yet another rotational probe design, an external motor can rotate a fiberoptic-based ultrathin probe (FIG. 6C).

Figure 7A:
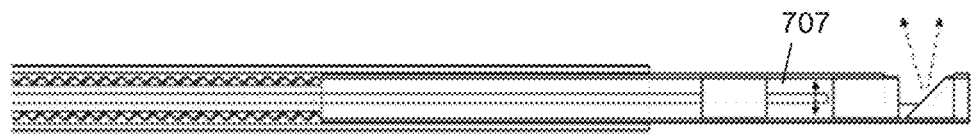
FIG. 7A shows another non-limiting embodiment of a linear scanning probe in a piezo-electronic tube.
Figure 7B:
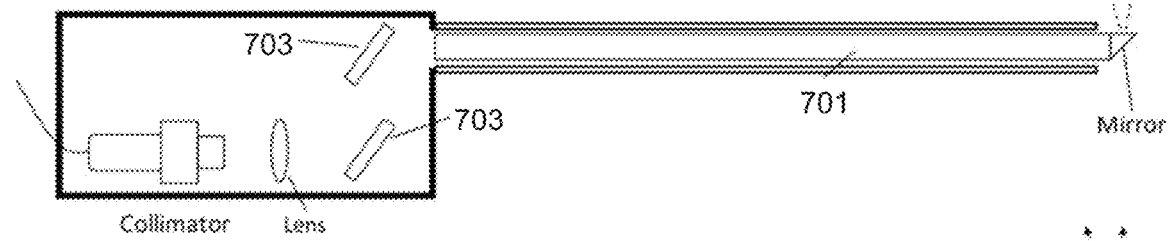
FIG. 7B shows a non-limiting embodiment of a linear scanning probe with a 2-axis galvanometer scanners.
Figure 7C:
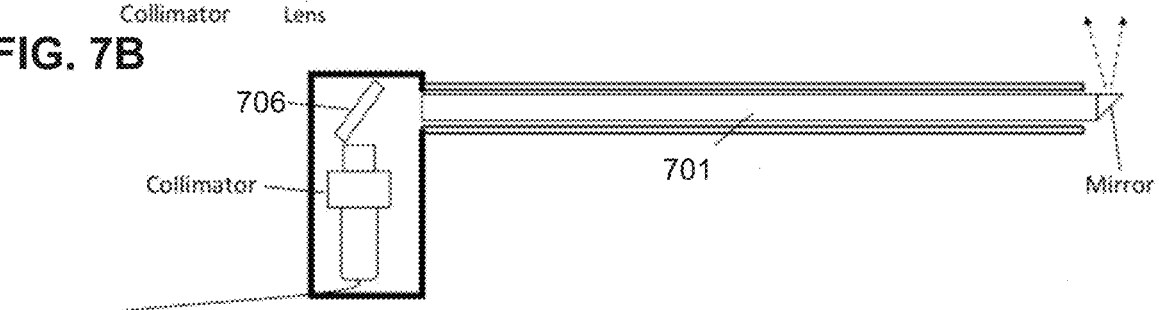
FIG. 7C shows a non-limiting embodiment of a linear scanning probe with a 2D MEMS mirror.

Referring to FIGS. 7A-7O, in some embodiments, a linear scanning scheme can be utilized. In one linear scanning probe design, as shown in FIG. 7A, a piezo-actuator may be attached to the distal end of the optical fiber in front of GRIN lens and rod mirror. The piezoactuator actuates the optical fiber to linearly scan the beam, thus allowing for linear scanning. In another linear scanning probe design, as shown in FIG. 7B, an OCT light is focused to a GRIN rod and a 2D MEMS mirror is utilized to obtain rapid two-dimensional scanning by actuating the 2D MEMS mirror. In yet another scanning probe design, as shown in FIG. 7O, an OCT light is focused to a GRIN rod and two galvanometer-actuated mirrors (703) are utilized to obtain rapid two-dimensional scanning.

Figure 8A:
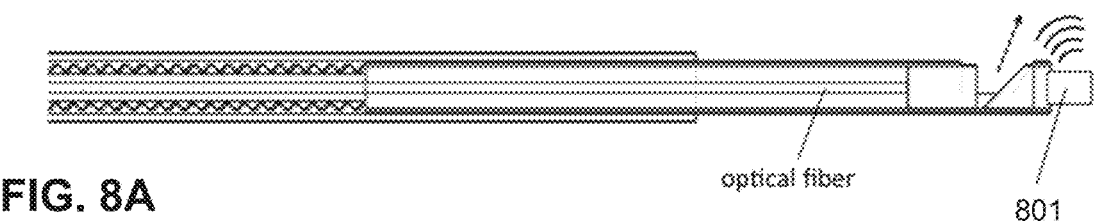
FIG. 8A shows a non-limiting embodiment of side-by-side OCT ultrasound (US) probe.
Figure 8B:
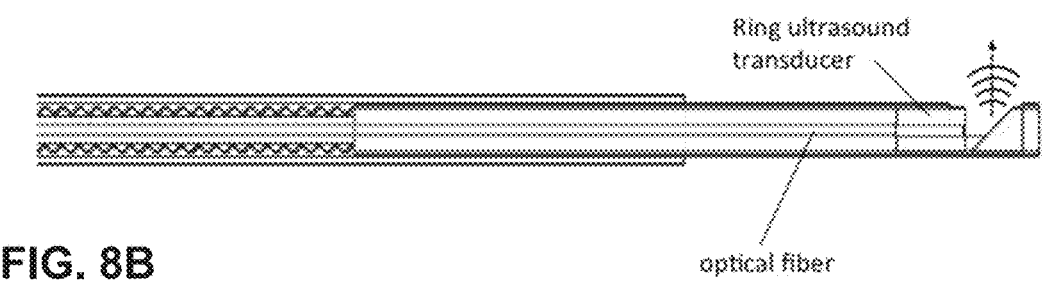
FIG. 8B shows a non-limiting embodiment of a co-axial OCT/US probe.

In some other embodiments; various other functionalities can be incorporated into the OCT probes. In one embodiment, an ultrasound transducer can be placed side-by-side or coaxially to the OCT beam (FIGS. 8A-8B). Ultrasound imaging, photoacoustic (PA) imaging, and optical coherence elastography (OCE) can be also achieved.

Figure 9:
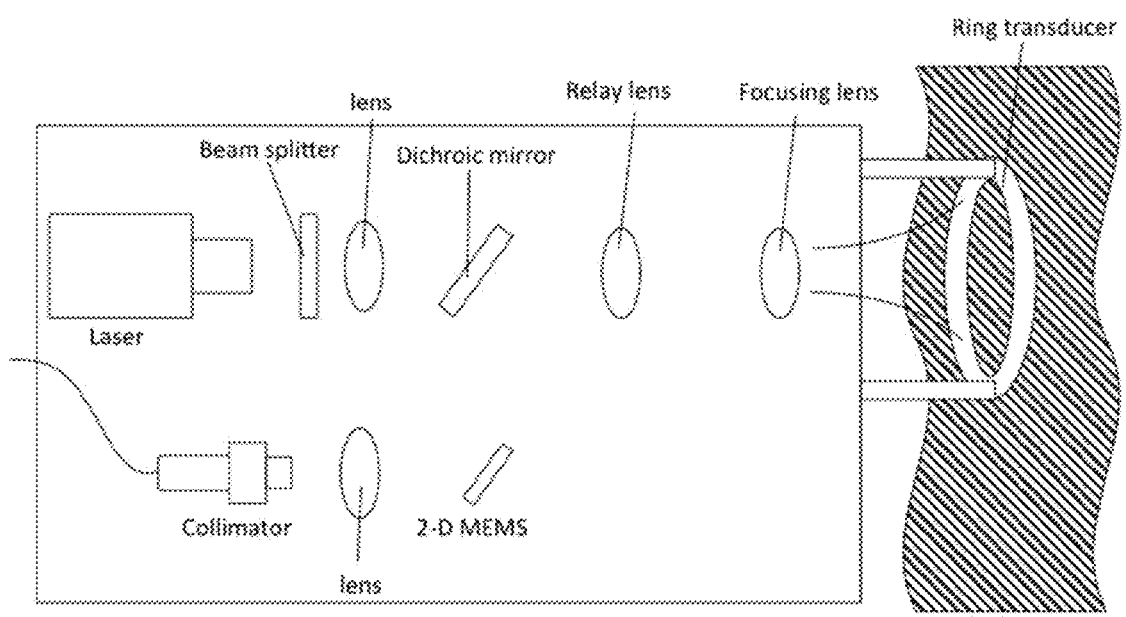
FIG. 9 shows a non-limiting embodiment of an external scanning probe for simultaneous treatment and diagnosis of the vulvovaginal wall.

In further embodiments, the present invention may also include an apparatus for imaging a surface of external genital skin (the vulva) and the uterine cervix during the treatment. Referring to FIG. 9, in one embodiment, the OCT probe may be coupled to the laser to monitor treatment. In another embodiment, a ring transducer can be placed on the surface of tissue to provide mechanical information.

Without wishing to limit the invention to a particular theory or mechanism, the present device may be capable of performing treatment and monitoring simultaneously. For instance, OCT imaging may be used to monitor micron level changes in the vaginal epithelium, lamina propria, muscularis and adventitia with superior resolution. At the same time, treatments using light and energy-based therapeutic probes can be performed based on, for example, $CO_2$ laser, Er:YAG laser, radio frequency (RF), High Intensity focused ultrasound (HiFU), and High Intensity Focused Electromagnetic (HiFEM). The treatment light can be any light between 10 nm-1 m wavelength and includes infrared, microwave, radiowave, visible light, and ultraviolet rays.

Figure 10:
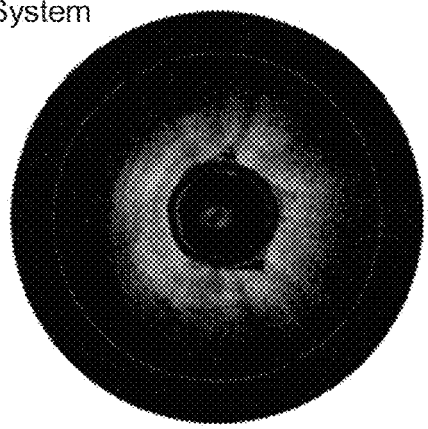
FIG. 10 shows non-limiting examples of OCT images of human vagina obtained by a 1.3 μm OCT system and a 1.7 μm OCT system.
Figure 10:
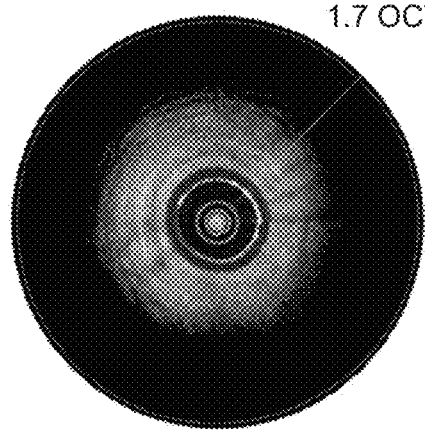
Figure 11:
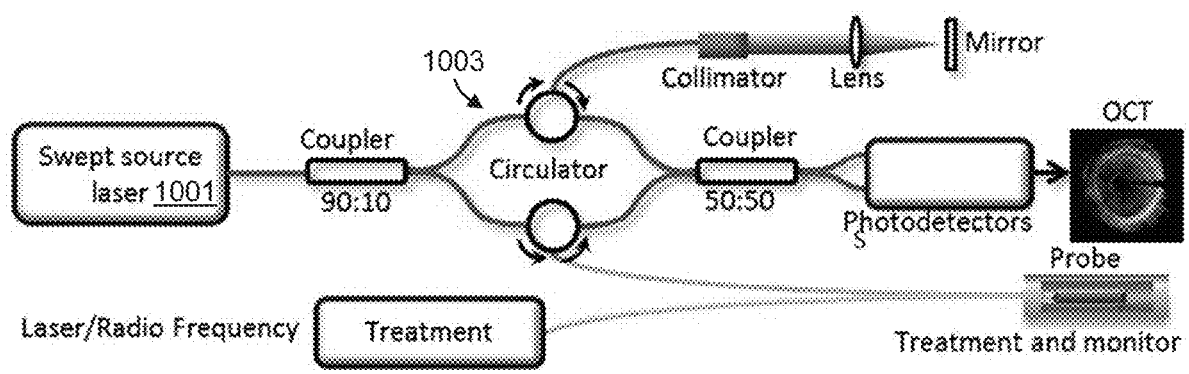
FIG. 11 shows a non-limiting embodiment of a combined OCT imaging system and treatment based on laser and radio frequency.

In some embodiments, the OCT system may include time domain and Fourier domain OCT. In other embodiments, the OCT system may be built based on spectrometer-based OCT or a Swept source laser-based OCT as shown in FIG. 11. In the OCT system, 90% of the laser power may be sent to the sample while 10% of the laser power may be sent to the reference mirror. A balanced photo detector and a data acquisition board can be used to detect and record the interference signal. The wavelength of OCT light can range from 400 nm-2000 nm. Typical OCT sources have wavelengths centered around 500 nm, 800 nm, 1 um, 1.3 um, or 1.7 um. Images taken by the OCT imaging system at wavelengths of 1.3 um and 1.7 um are shown in FIG. 10. Further still, the OCT imaging can include a Doppler OCT and/or a polarization sensitive OCT for visualization vasculature and tissue thermal damage.

For treatment monitoring, this present invention may also feature a multimodality imaging system that includes the OCT system. These combined systems may include integrated OCT/US (ultrasound imaging), OCT/Fluorescence or SHG (second harmonic generation), OCT/US/PA (photoacoustic imaging), OCT/US/Fluorescence, OCT/optical coherence elastography (OCE)/US and other multimodality imaging systems that include an OCT system.

Figure 12:
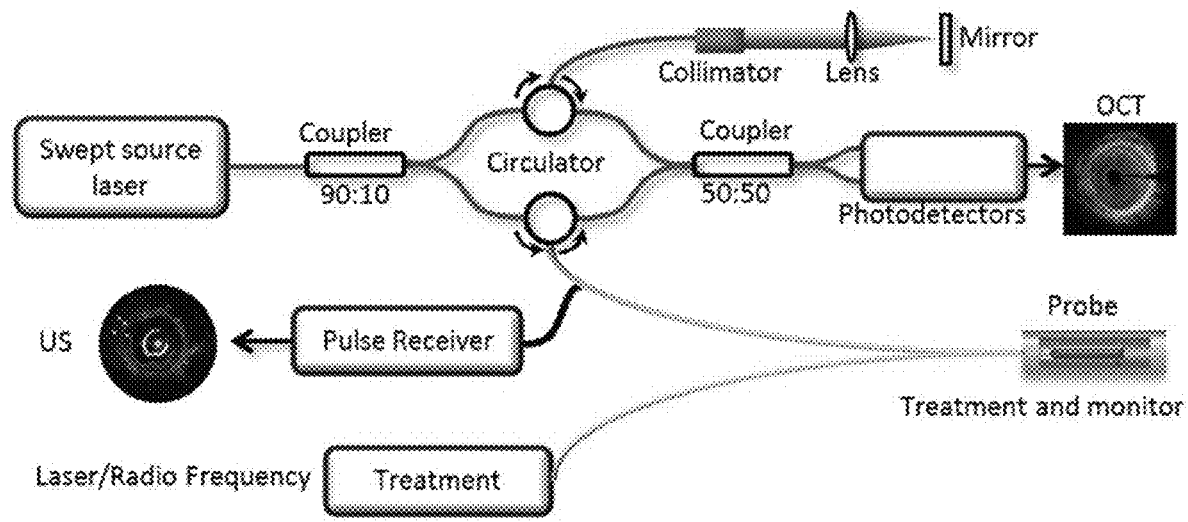
FIG. 12 shows a non-limiting embodiment of an integrated OCT/US imaging with treatment.

Referring to FIG. 12, in some embodiments, an integrated OCT/US may provide physician multi-scale structural information during and after the treatment. A trigger signal from the swept source laser is applied as the main trigger to synchronize the US imaging. For US imaging, a Pulser/Receiver is used to generate and detect ultrasound signal. In one embodiment, a US pulse transducer (801) is disposed on the distal end of the tube, and an ultrasound pulse receiver is configured to detect the ultrasound return signal. Without wishing to limit the invention to a particular theory or mechanism, the integrated OCT/US system is able to acquire OCT and US at the same time for monitoring the treatment with superior resolution and large imaging depth.

Figure 13:
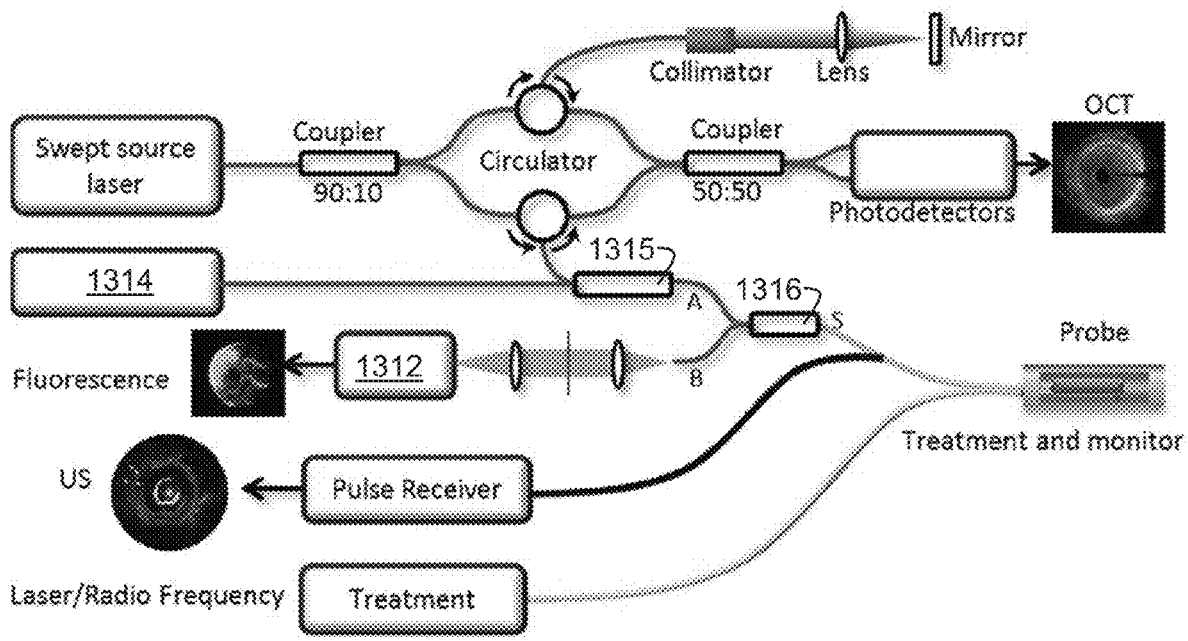
FIG. 13 shows a non-limiting embodiment of an integrated OCT/US/Fluorescence with treatment.

Referring to FIG. 13, in one embodiment, an integrated OCT/Fluorescence/US imaging may provide physician multi-scale structural information as well as molecular information during and after the treatment. A trigger signal from the swept source laser is applied as the main trigger to synchronize the US and fluorescence imaging. A wavelength division multiplexer may be used to combine the OCT and fluorescence imaging systems. For the fluorescence imaging system, a double clad fiber (DCF) coupler may be used to collect the emission light, which can also apply free space optical path to combine OCT and fluorescence, and collect emission light. A laser diode may be used as the excitation source and a DCF coupler may be incorporated to transmit excitation light and collect emission light. The emission light can return through the DCF coupler, then filtered by a filter and detected by a photomultiplier tube for fluorescence imaging. For ultrasound imaging, a Pulser/Receiver may be used to generate and detect ultrasound signals. Without wishing to limit the invention to a particular theory or mechanism, the integrated OCT/US/Fluorescence system may be able to acquire OCT, fluorescence, and US at the same time and same location with superior resolution, large imaging depth, and molecular properties.

Figure 14:
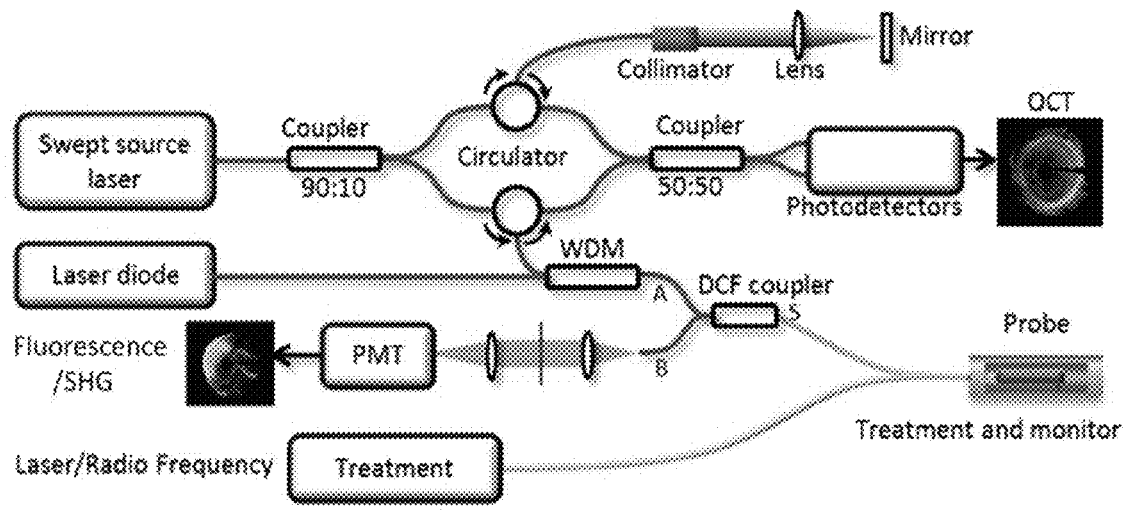
FIG. 14 shows a non-limiting embodiment of an integrated OCT/Fluorescence with treatment.

Referring to FIG. 14, in some other embodiments, an integrated OCT/Fluorescence/SHG imaging may provide physician high resolution structural information about the normal pattern at various age groups, pre- and post-menopausal, as well as the molecular information during and after various treatment modalities and protocols. A trigger signal from the swept source laser is applied as the main trigger to synchronize fluorescence. A wavelength division multiplexer (1315) may be used to combine the OCT and fluorescence imaging systems. For the fluorescence imaging system, a double clad fiber (DCF) coupler (1316) may be used to collect the emission light, which can also apply free space optical path to combine OCT and fluorescence, and collect emission light. For fluorescence imaging, a laser diode (1314) may be used as the excitation source and a DCF coupler (1316) may be incorporated to transmit excitation light and collect emission light. The emission light can come back through DCF coupler, then filtered by a filter and detected by a photomultiplier tube (PMT) (1312) for fluorescence imaging. For example, when the device is used, the laser diode (1314) emits light capable of exciting florescence, and the laser diode light (1314) and the beam of the swept source laser or broad band light source are combined by the wavelength division multiplexer (1315). The DCF coupler (1316) transmits the combined beam into the imaging probe, and the return signal from the probe is received by the DCF coupler (1316). The emission light from the DCF coupler is then detected by the PMT (1312) for fluorescence imaging. Without wishing to limit the invention to a particular theory or mechanism, the integrated OCT/Fluorescence/SHG system may be able to acquire OCT, Fluorescence/SHG at the same time and same location with superior resolution, and molecular properties.

Figure 15:
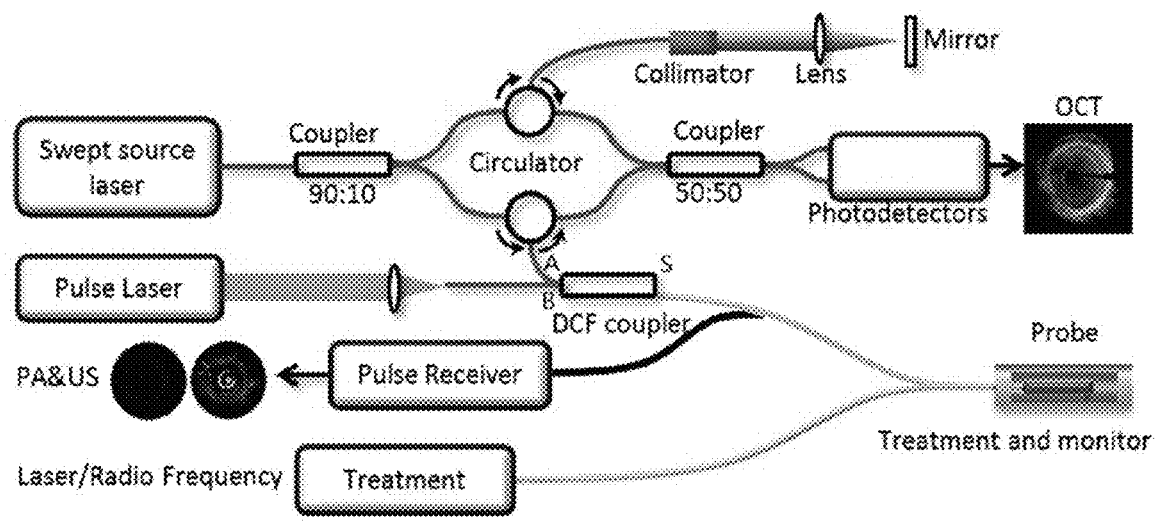
FIG. 15 shows a non-limiting embodiment of an integrated OCT/photoacoustic (PA)/US with treatment.

Referring to FIG. 15, in yet other embodiments, an integrated OCT/PA/US imaging may provide physician multi-scale structural information as well as the molecular information without injecting any contrast agent during and after the treatment. A trigger signal from the swept source laser may be applied as the main trigger to synchronize the US and PA imaging. For ultrasound imaging, a Pulser/Receiver can be used to generate and detect ultrasound signal. For PAT, a pulsed laser can used to excite tissue to generate a PAT signal, and a Pulser/Receiver can be used to accept the PA signal. In one embodiment, a delay for the Pulser/Receiver may be applied to separate PA and US. In an alternative embodiment, two Pulser/Receivers may be used for each of the PA and US. Without wishing to limit the invention to a particular theory or mechanism, the integrated OCT/US/PAT system may be able to acquire OCT. US, and PA at the same time and same location with superior resolution, large imaging depth, and molecular properties.

Figure 16:
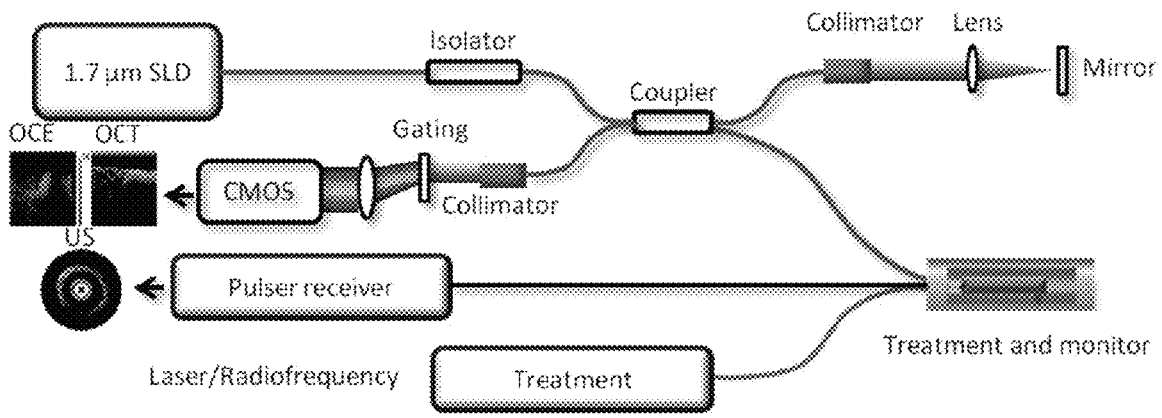
FIG. 16 shows a non-limiting embodiment of an integrated OCT/OCE/US with treatment.
Figure 17A:
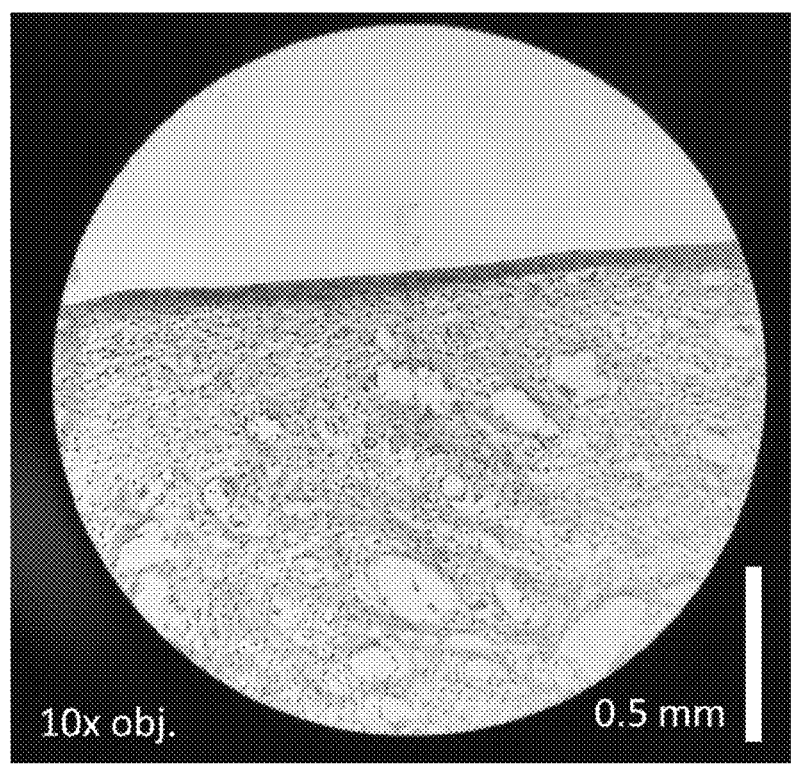
FIG. 17A shows a histology of human vaginal tissue.
Figure 17B:
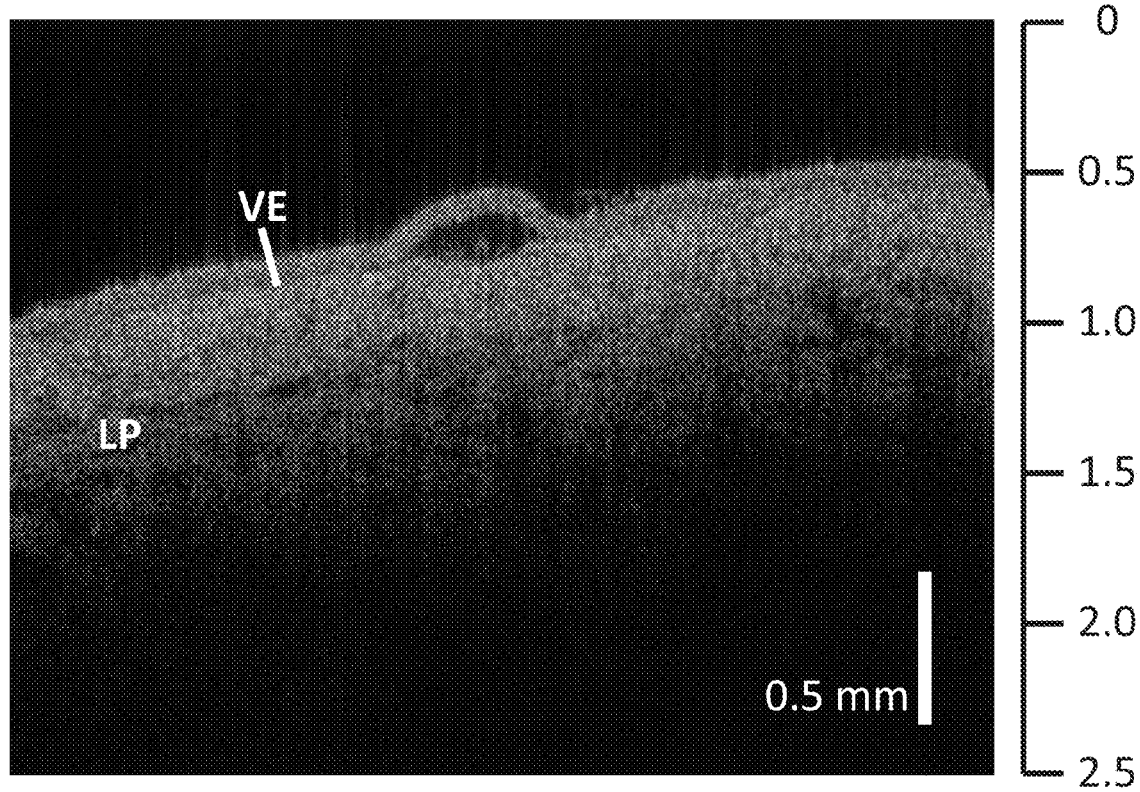
FIG. 17B shows an OCT image that captures the structure 1 mm below surface, including vaginal epithelium, lamina propria, and blood vessels, which matches well with the histology in FIG. 17A.
Figure 18A:
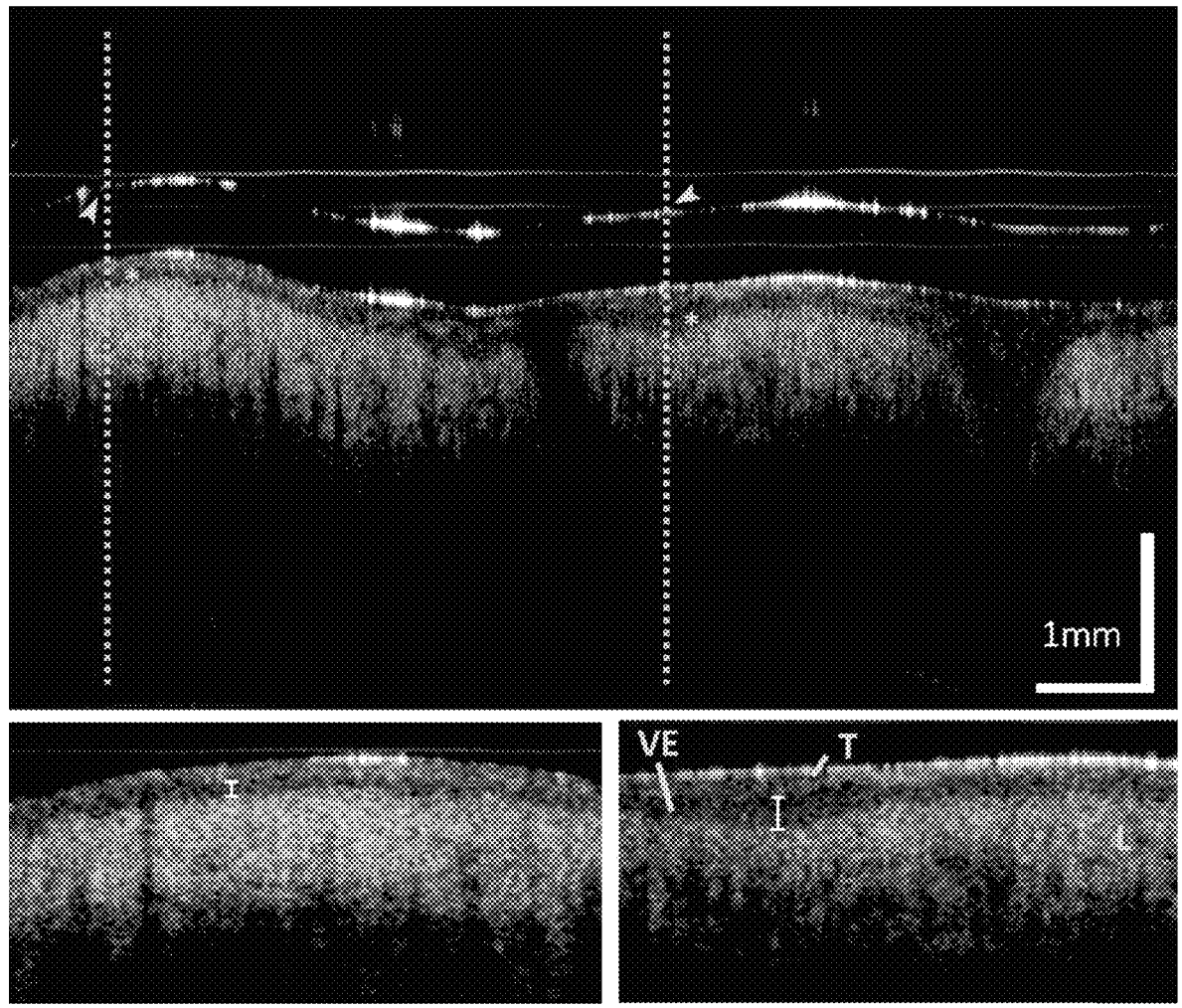
FIG. 18A shows in vivo OCT images of human vaginal tissue which provide precise epithelium thickness measurement in real time.
Figure 18B:
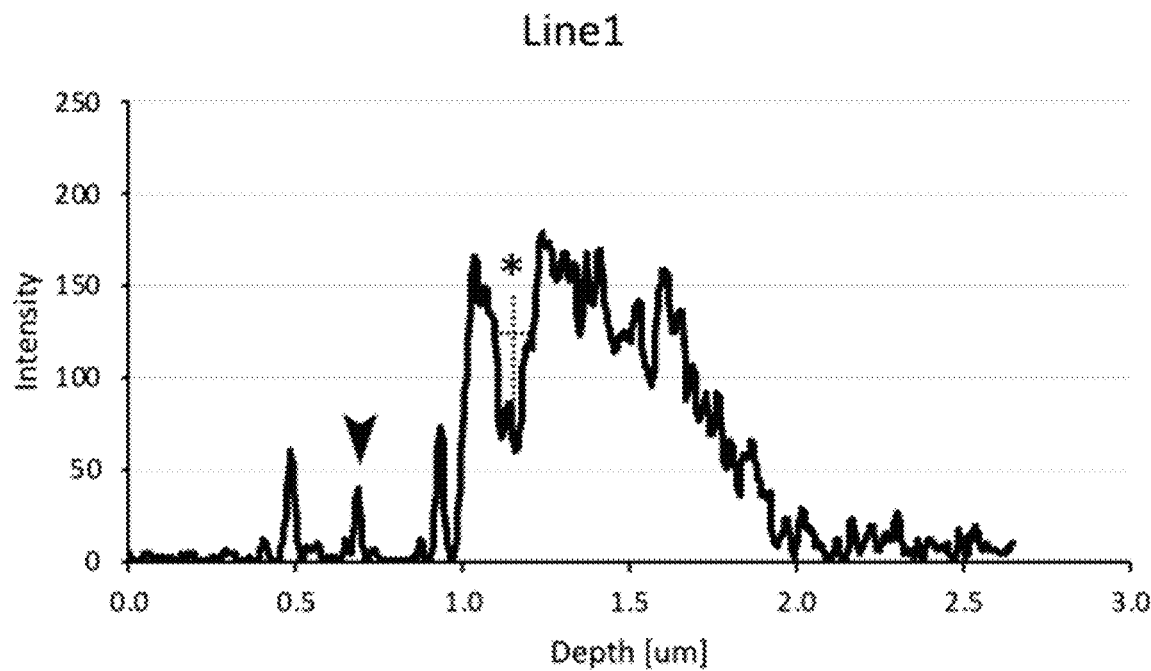
FIG. 18B is a graph of an OCT intensity profile of the left vertical dotted line in FIG. 18A.
Figure 18C:
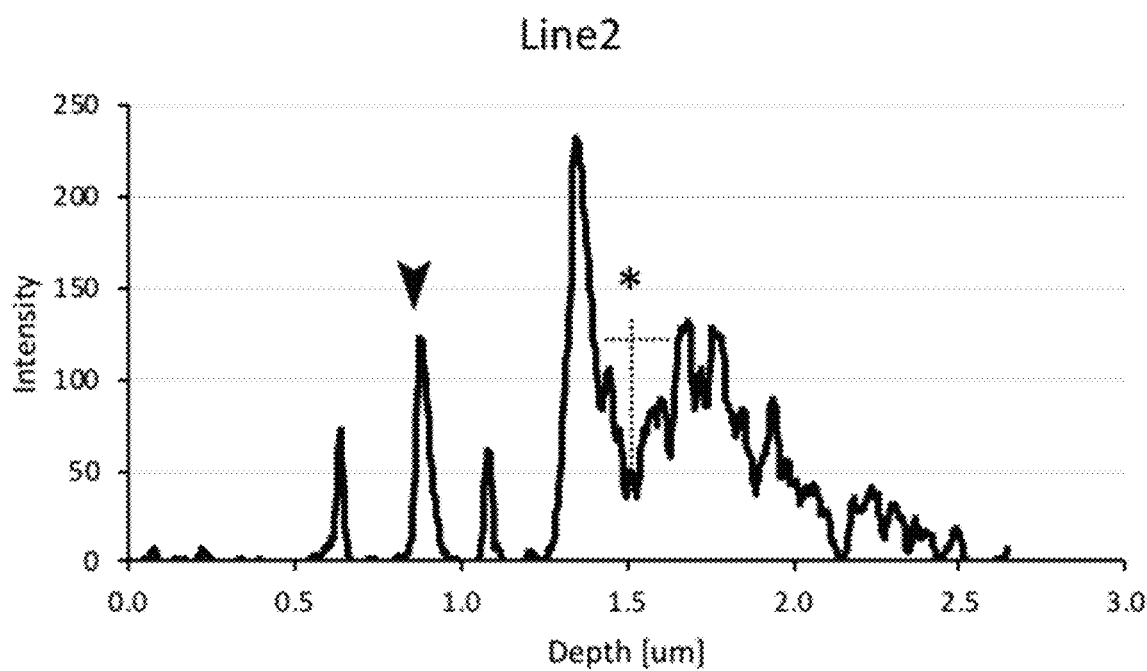
FIG. 18C is a graph of an OCT intensity profile of the right vertical dotted line in FIG. 18A.
Figure 19A:
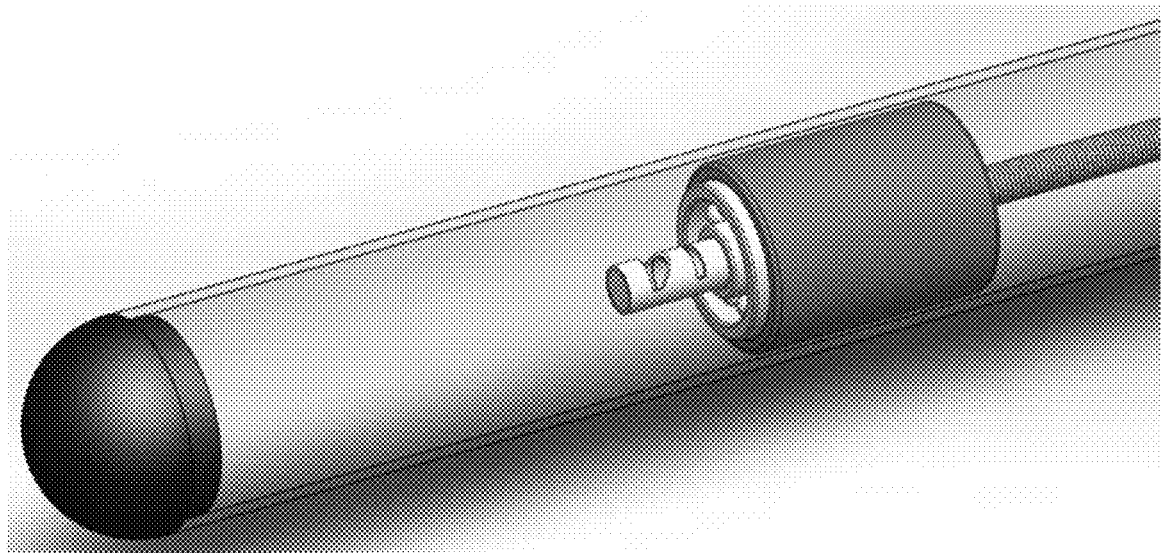
FIGS. 19A-19B show a non-limiting example of an intravaginal OCT endoscopy probe and use thereof.
Figure 19B:
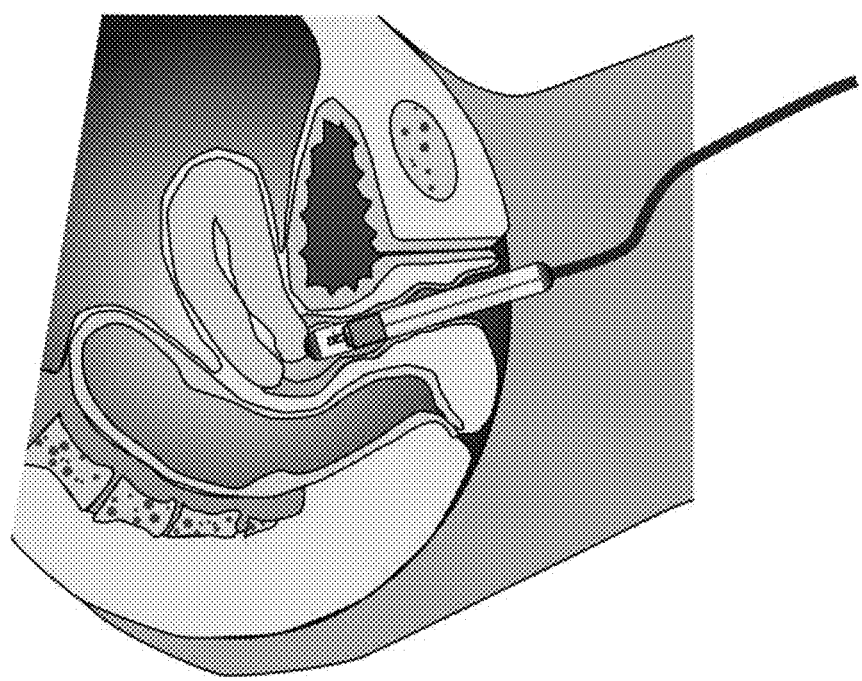
Figure 20A:
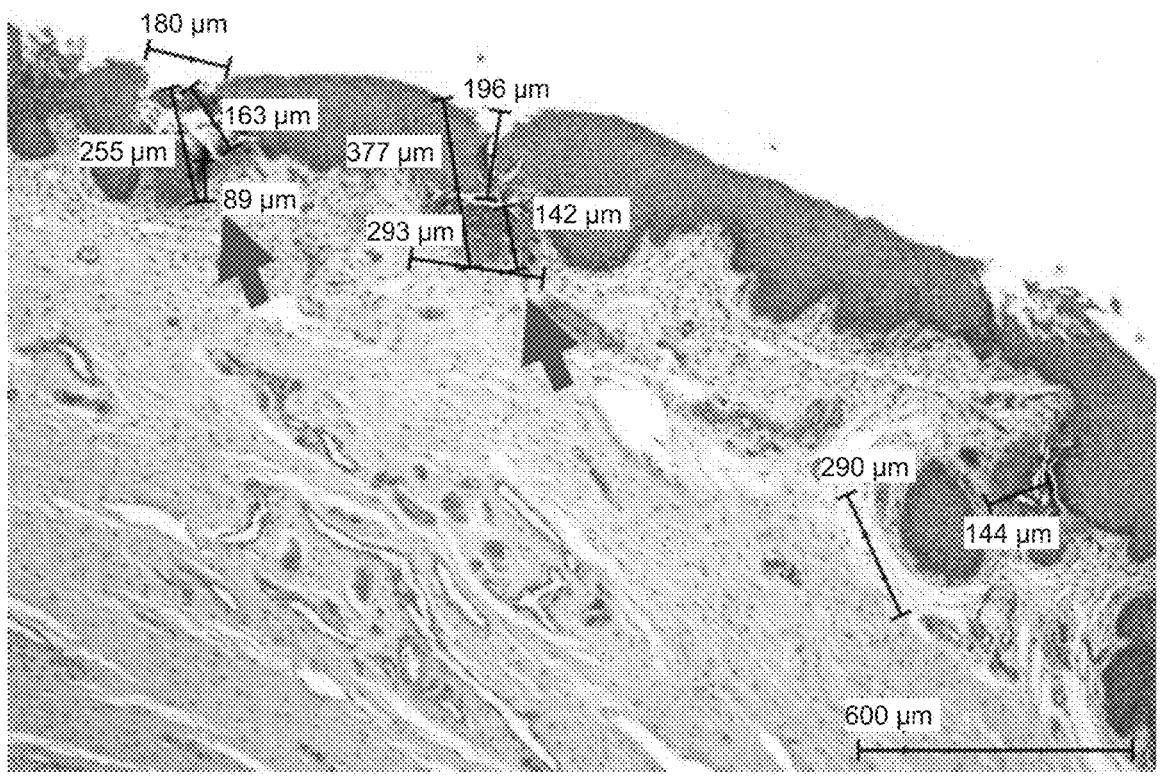
FIGS. 20A-20E show histology of pig vagina after ablation laser treatment.
Figure 20B:
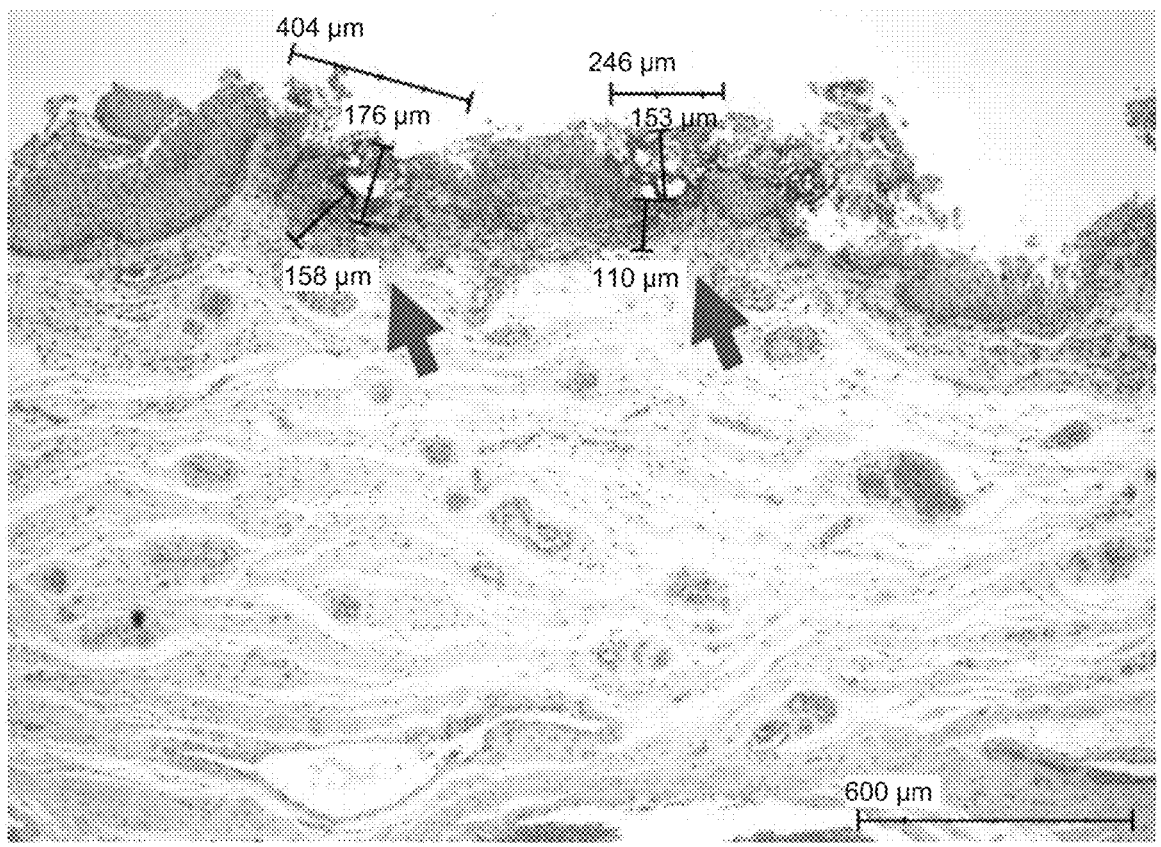
Figure 20C:
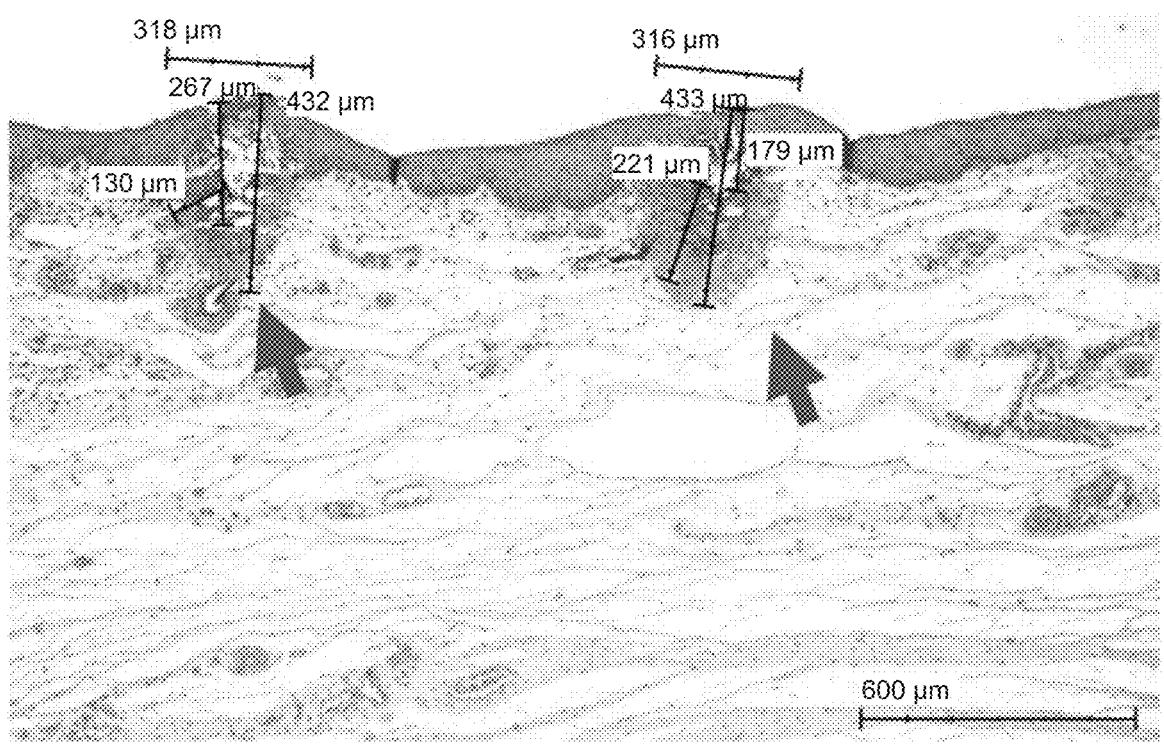
Figure 20D:
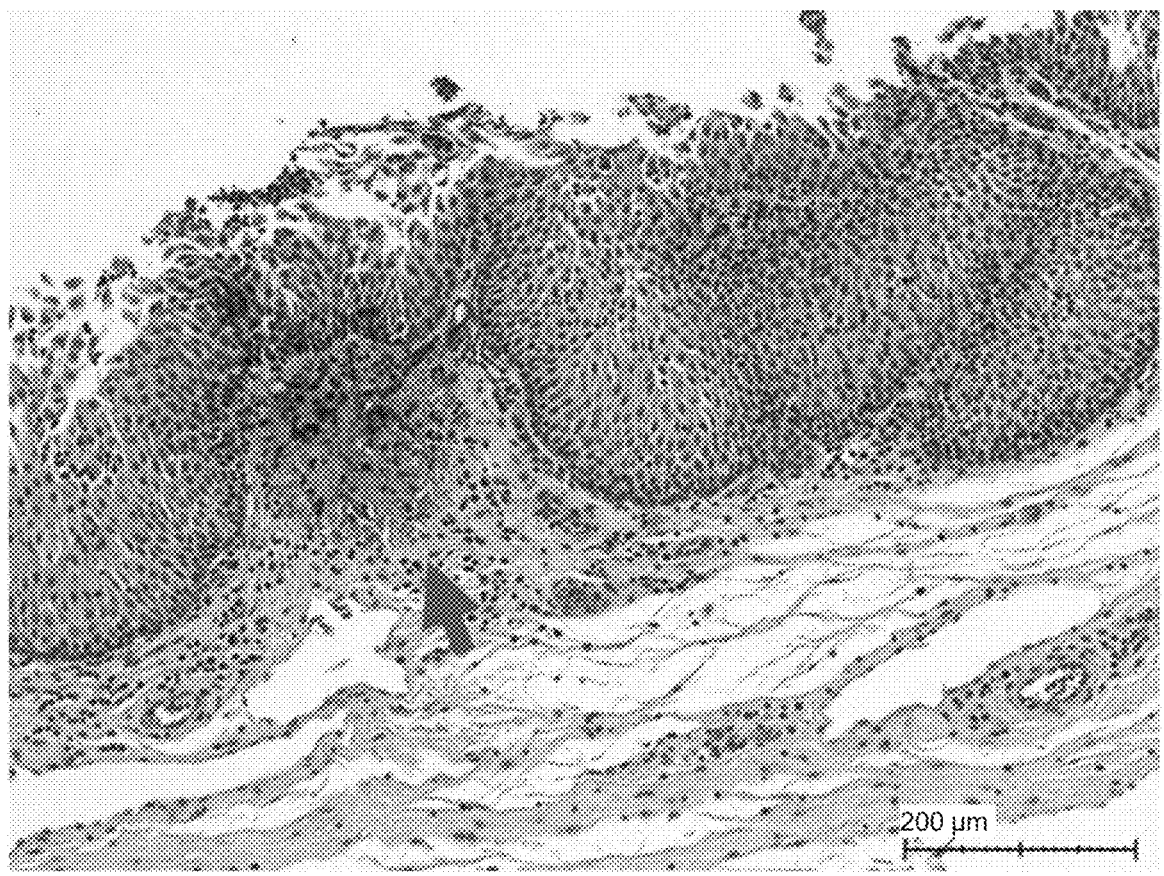
Figure 20E:
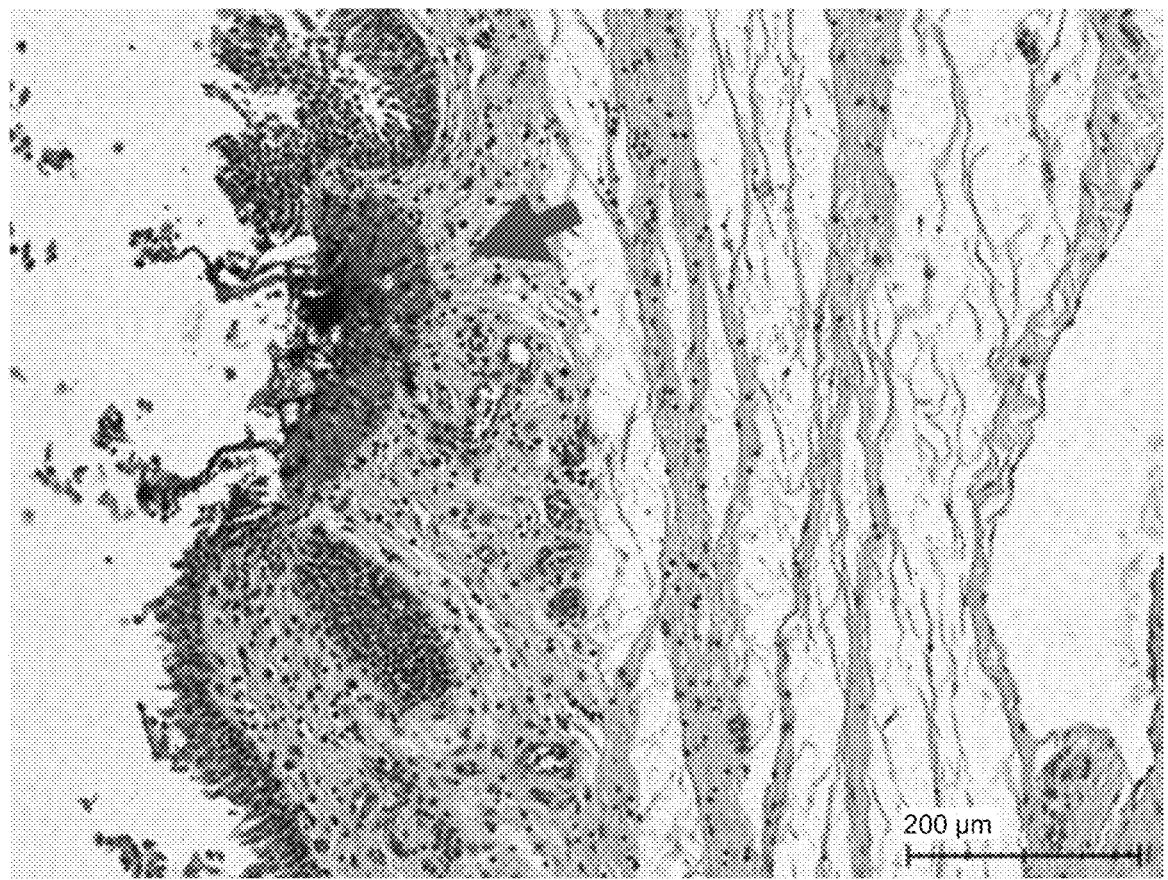
Figure 21A:
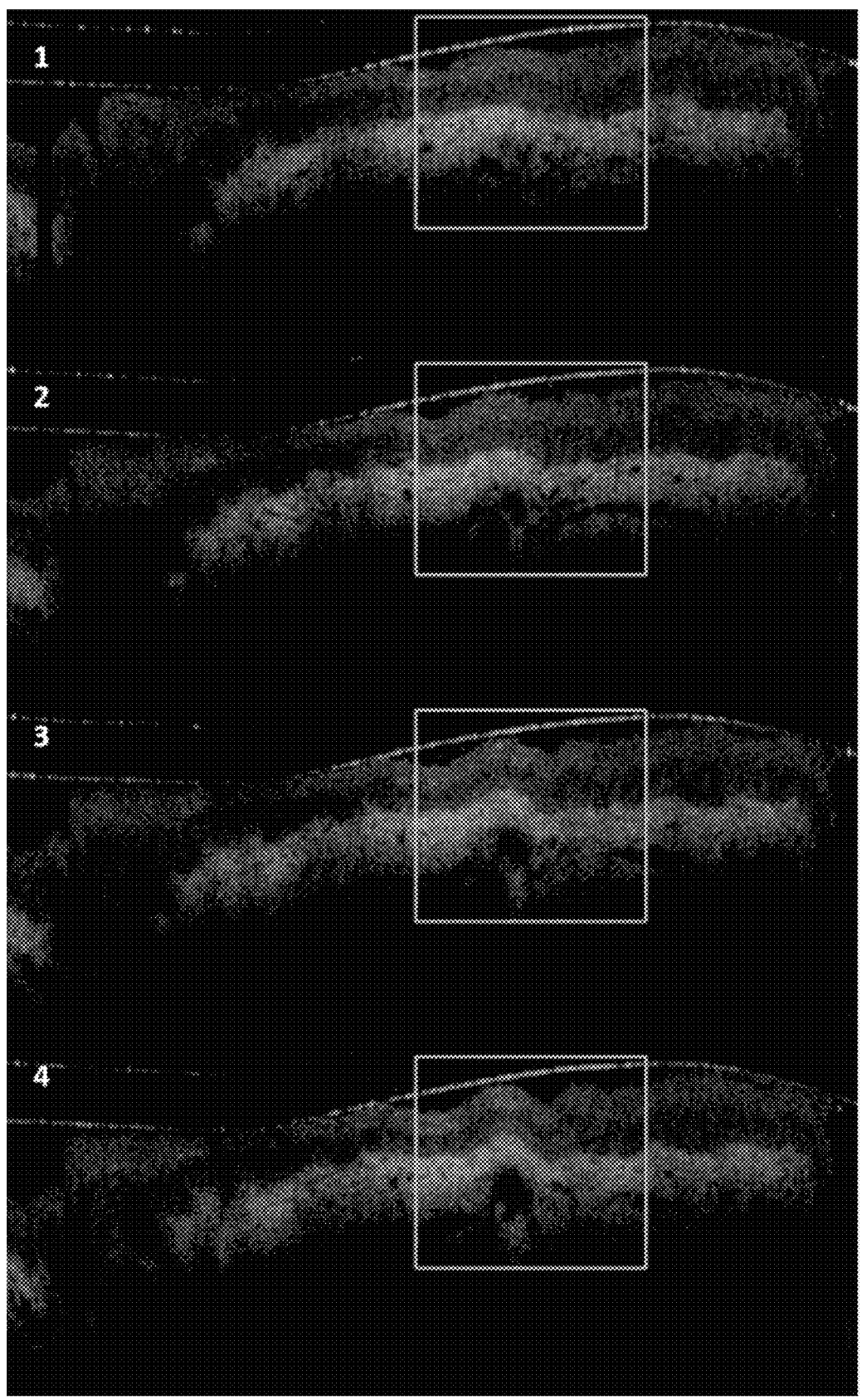
FIGS. 21A-21O show in vivo OCT images of a post-laser patient.
Figure 21B:
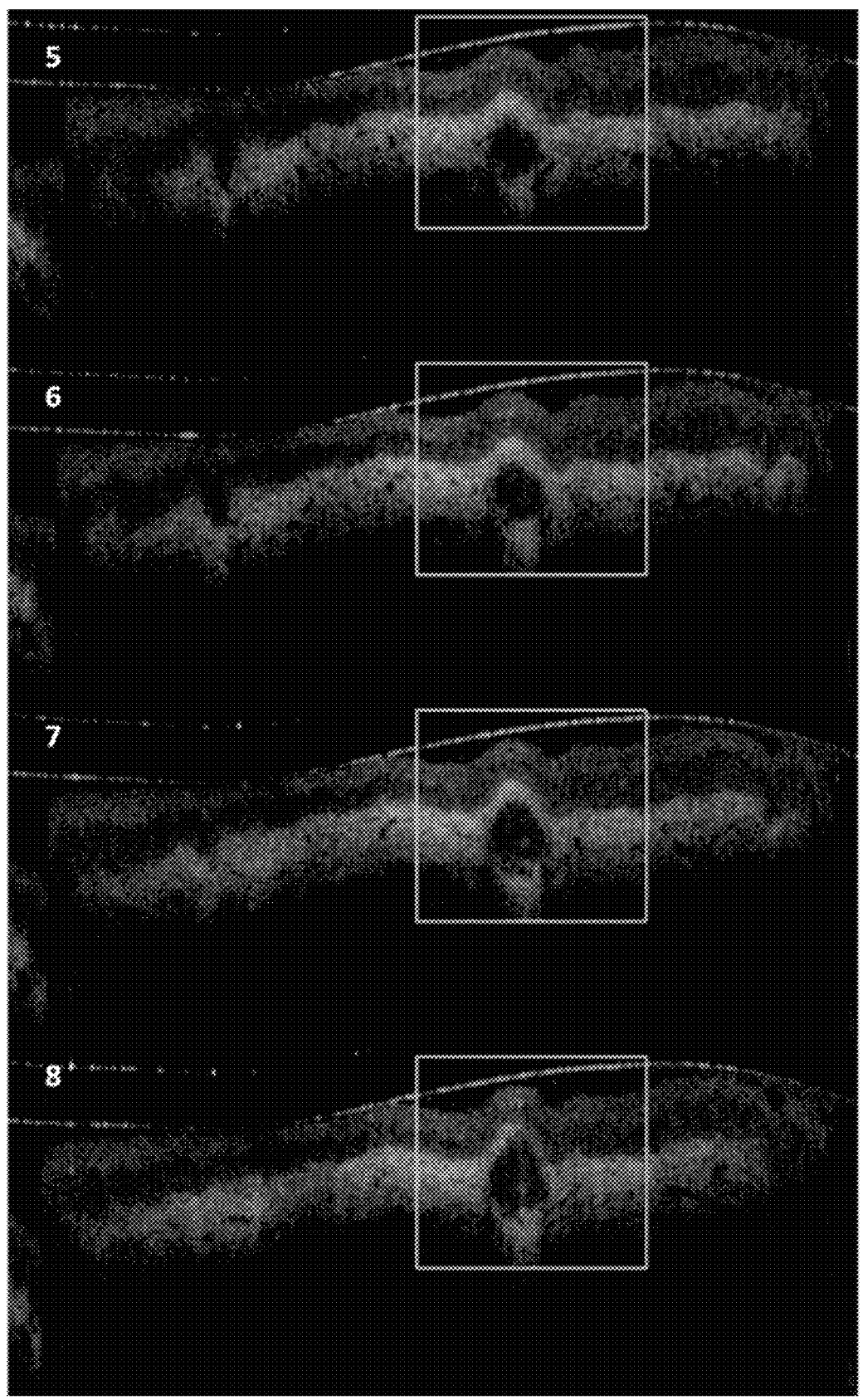
Figure 21C:
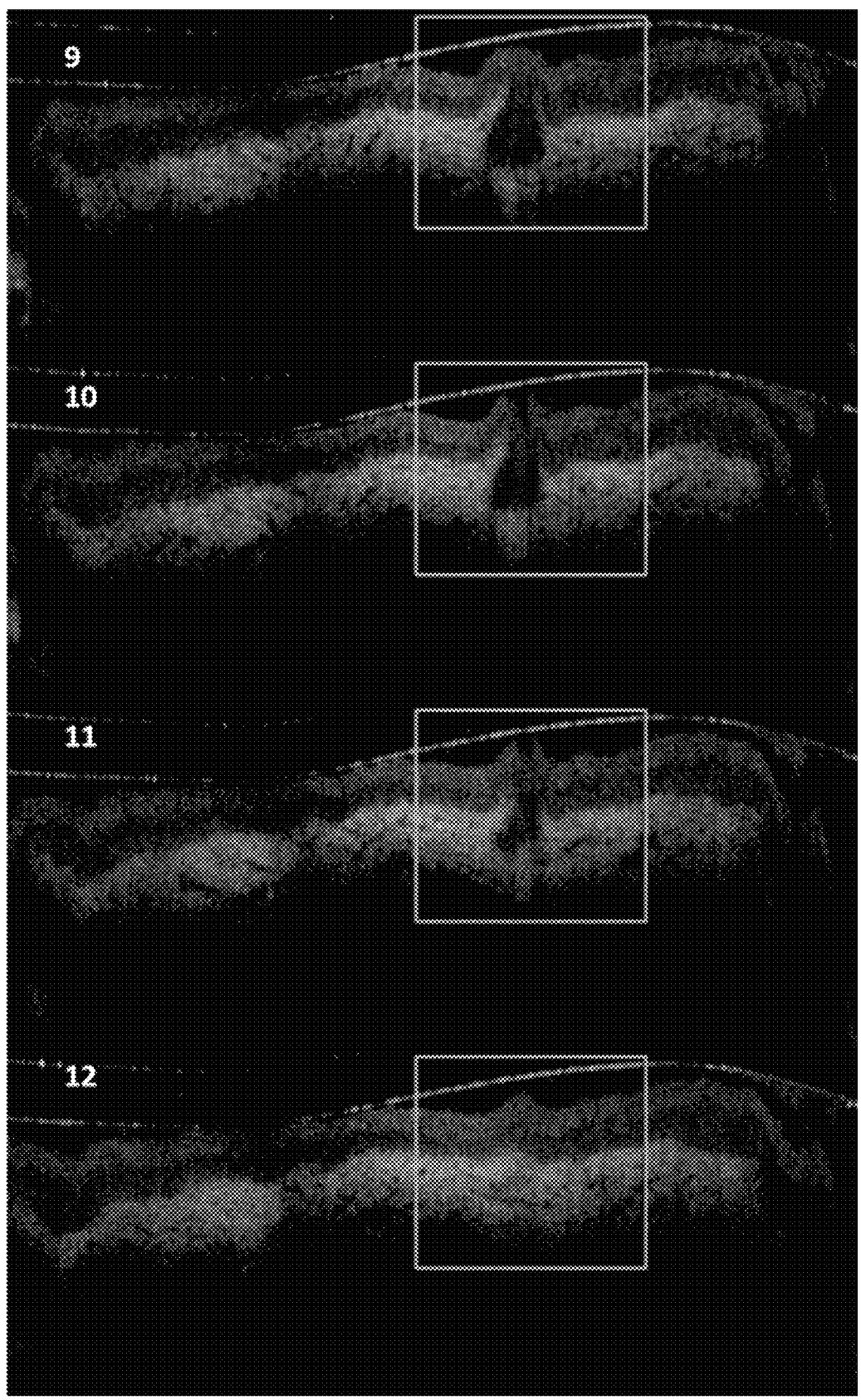
Figure 22A:
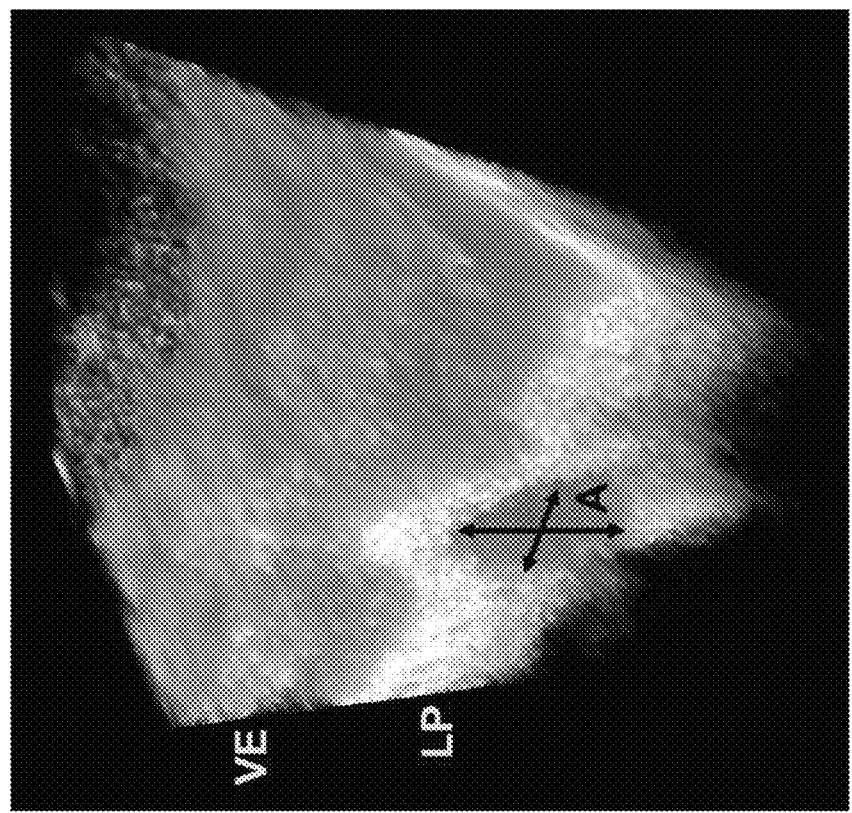
FIG. 22A is a 3D visualization of vaginal tissue post-laser treatment.
Figure 22A:
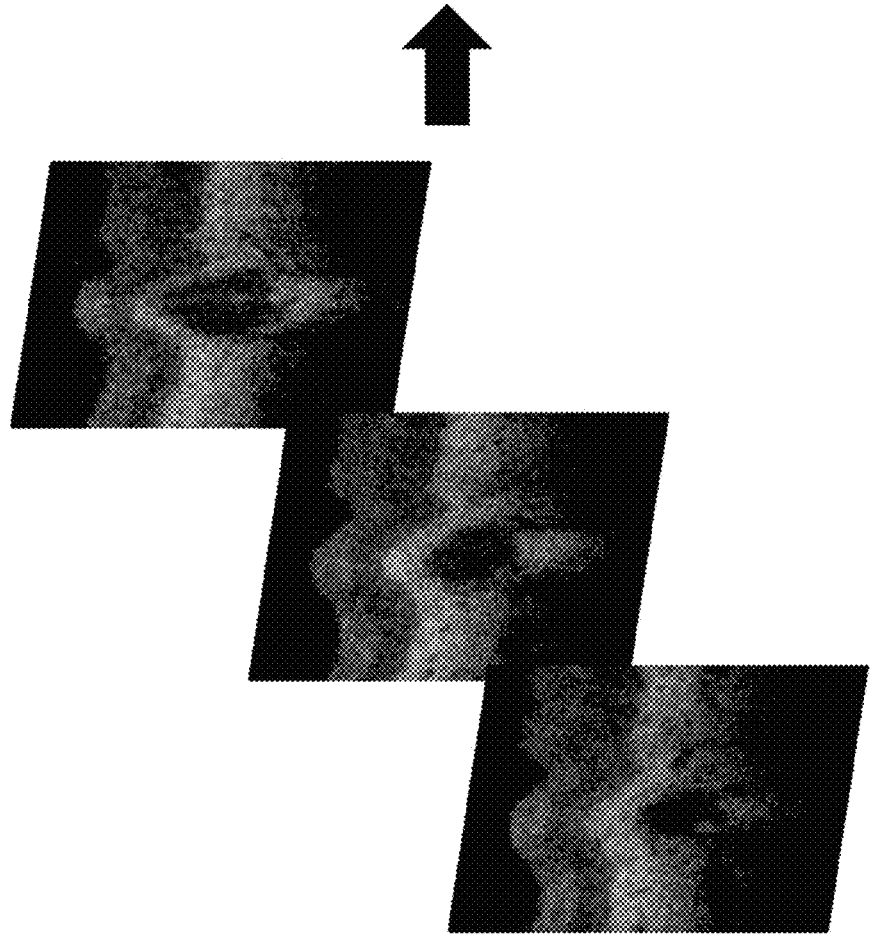
Figure 22B:
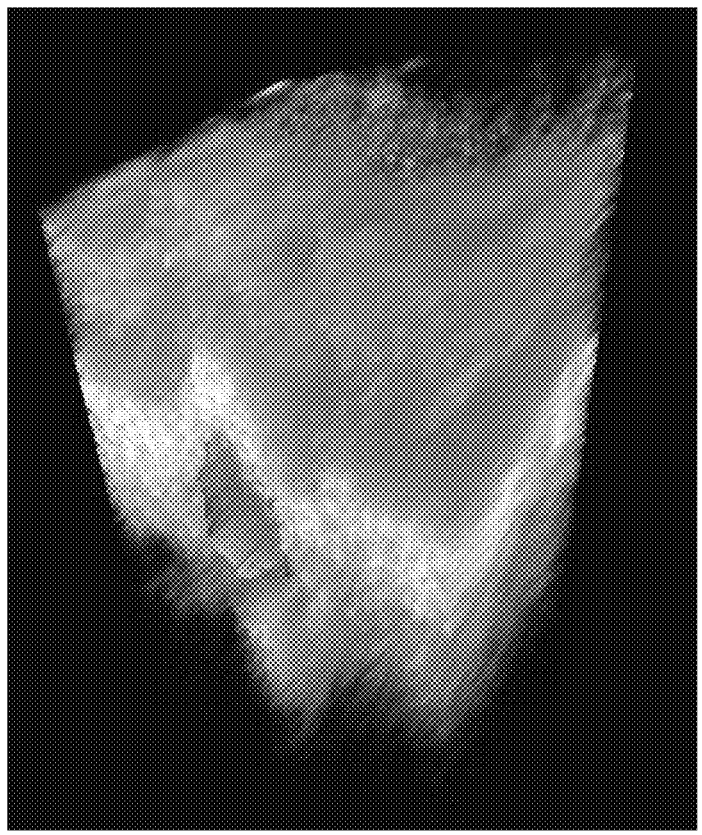
FIGS. 22B-22C depict segmentation of an ablation region to provide precise dimensions of the affected tissue.
Figure 22C:
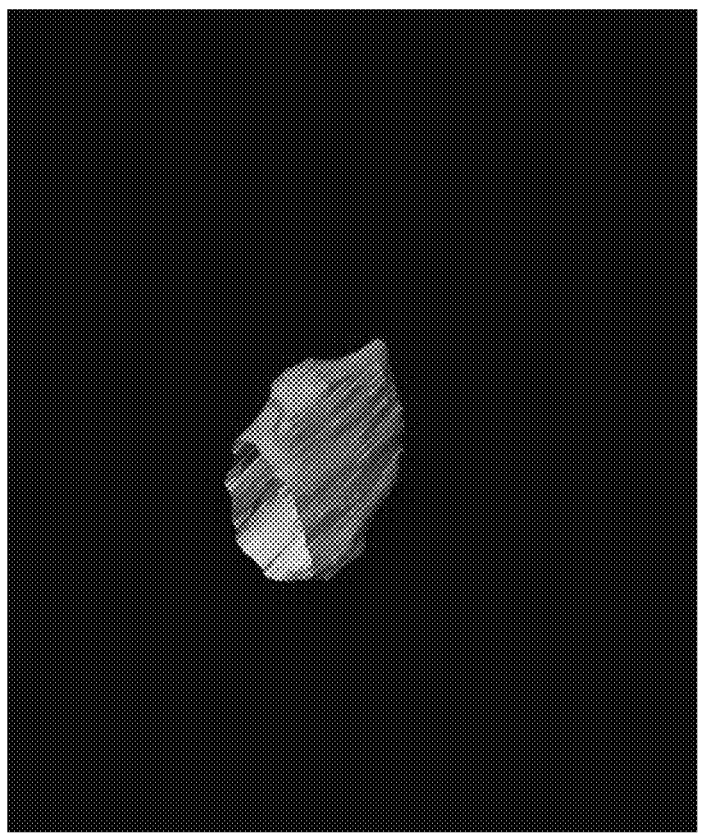
Figure 23:
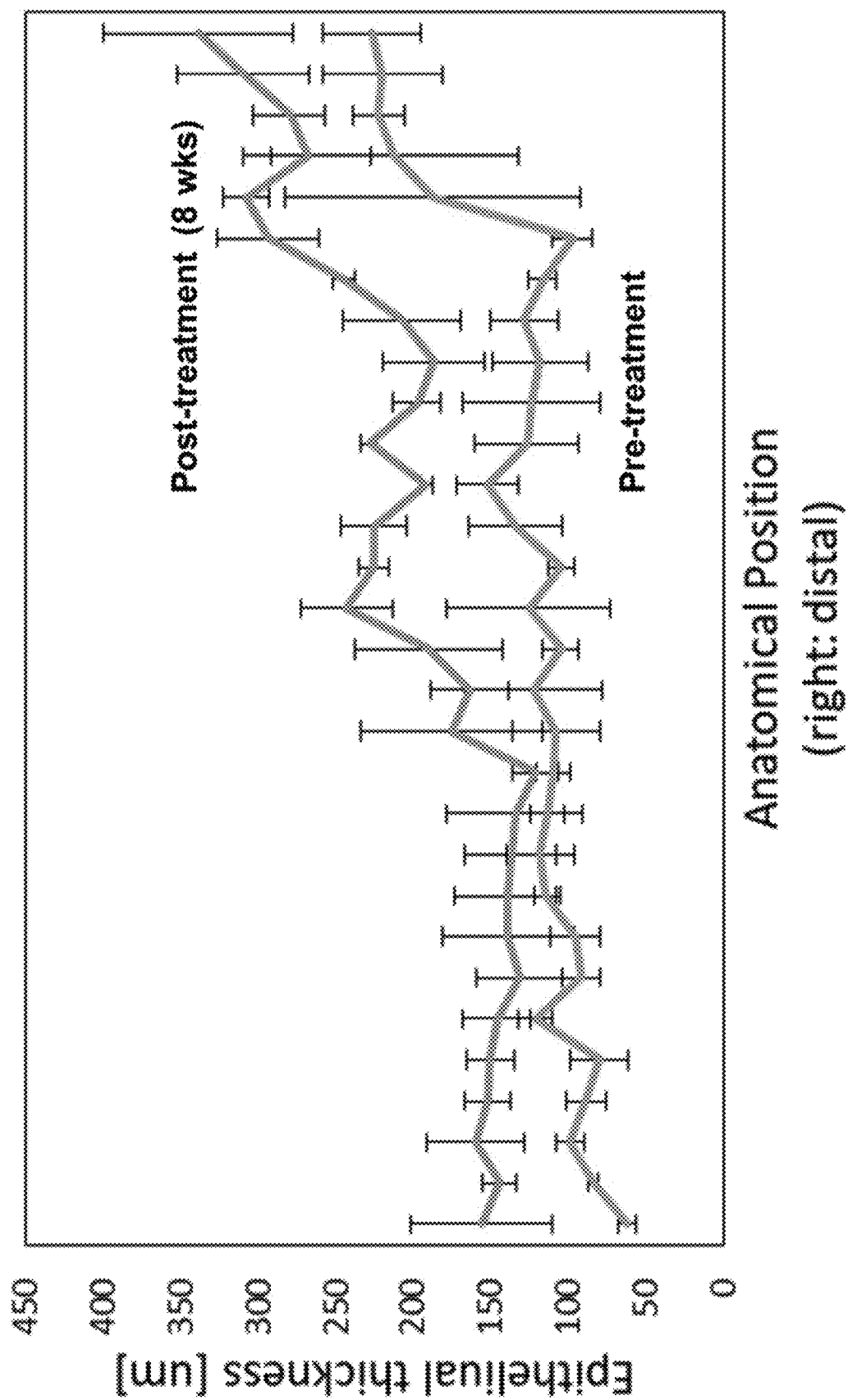
FIG. 23 is a graph of epithelial thickening post $CO_2$ fractional laser treatment.

Referring to FIG. 16, in further embodiments, an integrated OCT/OCE/US imaging may provide physician multi-scale structural information as well as the mechanical properties information at various age groups, pre- and post-menopausal women, without injecting any contrast agent during and after the treatment. A trigger signal from the swept source laser is applied as the main trigger to synchronize the US and OCE imaging. For ultrasound imaging, a Pulser/Receiver is used to generate and detect ultrasound signal. In addition, the pulser/receiver is also used to excite the tissue for OCE imaging. In one embodiment, a delay for the Pulser/Receiver may be applied to separate OCE and US. In an alternative embodiment, two Pulser/Receivers may be used for each of the OCE and US. Without wishing to limit the invention to a particular theory or mechanism, the integrated OCT/US/OCE system may be able to acquire OCT, US, and OCE at the same time and same location with superior resolution, large imaging depth, and biomechanical properties.

As used herein, the term "about" refers to plus or minus 20% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A device for the simultaneous treatment and monitoring of pelvic floor disorders, combining optical tomography and energy based therapeutic treatment into a combined probe, comprising:
    a. a treatment device capable of emitting a treatment beam (113), comprising:
        i. a first glass tube for housing the treatment device;
        ii. a mirror (104) disposed the distal end of the first glass tube so as to reflect light directed from the proximal end of the tube outward through the tube;
        iii. a treatment laser (101) disposed within the proximal end of the first glass tube;
        iv. a pixel beam splitter (102) disposed within the tube so as to be in a light pathway of the treatment laser; and
        v. at least one lens (103) disposed between the pixel beam splitter and the mirror so as to focus light from the pixel beam splitter into the mirror (104),
        wherein the treatment laser emits a light beam which is directed into the pixel beam splitter, wherein the pixel beams are directed into the lens, wherein the beams are focused on the mirror, wherein the mirror reflects the beams out of the tube;
    b. an imaging probe (105) disposed on a side of the treatment device, capable of detecting an interference signal, said imaging probe (105) comprising:
        i. a second glass tube (112) for housing the imaging probe;
        ii. a micro-motor (111) disposed within a distal end of the second glass tube and controlled by a motor driver;
        iii. a rod mirror (110) mounted on the motor;
        iv. an optical fiber (108) disposed within a proximal end of the second glass tube, oriented so as to direct light into a focusing lens;
        v. the focusing lens (109) disposed so as to direct laser light from the optical fiber (108) into the rod mirror; and
        vi. a metal housing (106);
    c. a disposable, optically clear tube cover (107) enclosing the treatment device and the imaging probe (105) into a single contained device;
    d. a swept source laser or broad band light source, capable of generating light for performing optical coherence tomography (OCT);
    e. a photo detector, used to detect the interference signal;
    f. a fiber optic circulator (1003), optically connected to the swept source laser or broad band light source, and to the photo detector, and to the optical fiber of the imaging probe, capable of acting as a non-reciprocating one-directional three-port device to sequentially direct light from the swept source laser or broad band light source (1001) to the imaging probe, and direct a reflected interference signal from the imaging probe to the photo detector;

g. a motor control board, used to drive the micro-motor of the imaging probe; and h. a data acquisition board, operatively connected to a communication port of the swept source laser or broad band light source and the photo detector, capable of receiving a timing signal from the laser or broad band light source and recording the interference signal at the beginning of every sweep cycle;

wherein the fiber optic circulator directs light from the swept source laser or broad band light source into the imaging probe (105), wherein the light is transmitted through the focusing lens (109) to the rod mirror (110), and out into the tissue, wherein the micro-motor (111) rotates the rod mirror (110) to direct the light, wherein after passing through tissue, light is reflected back into the rod mirror (110), wherein the light is directed into the optical fiber (108), wherein the fiber optic circulator directs the light into the photo detector, wherein the photo detector receives the light and transmits a signal to the data acquisition board, which records the signal.

2. The device of claim 1, further comprising an ultrasound (US) pulse transducer (801), disposed on the distal end of the tube, and an ultrasound pulse receiver, capable of detecting the ultrasound return signal, wherein a trigger signal from the swept source laser or broad band light source is applied as the main trigger to synchronize US imaging.

3. The device of claim 1, further comprising a fluorescence imaging apparatus, comprising:

a. a laser diode (1314), used as the excitation source;

b. a wavelength division multiplexer (1315), used to combine the beam from the swept source laser or broad band light source and the laser diode;

c. a double clad fiber (DCF) coupler (1316), used to transmit and receive emission light received from the imaging probe; and d. a photomultiplier tube (PMT) (1312), used to detect emission light;

wherein the laser diode emits light capable of exciting florescence, wherein the laser diode light and the beam of the swept source laser or broad band light source are combined by the wavelength division multiplexer, wherein the DCF coupler transmits the combined beam into the imaging probe, wherein the return signal from the probe is received by the DCF coupler, wherein the emission light from the DCF coupler is detected by the PMT for fluorescence imaging.

4. The device of claim 1, further comprising a second harmonic generation (SHG) imaging apparatus.

5. The device of claim 1, further comprising a photoacoustic (PA) imaging apparatus.

6. The device of claim 1, further comprising an optical coherence elastography (OCE) imaging apparatus.

7. The device of claim 1, wherein the imaging probe is a fiberoptic probe or a linear scanning probe.

8. The device of claim 7, wherein the linear scanning probe further comprises a piezoactuator (707) disposed at the distal end of the probe, in front of a gradient-index (GRIN) optics lens (701) and rod mirror, wherein the piezoactuator actuates the optical fiber to linearly scan the beam.

9. The device of claim 7, wherein the linear scanning probe comprises a gradient-index (GRIN) optics lens (701) and a 2D MEMS mirror (706), wherein the 2D MEMS mirror is actuated to produce two-dimensional scanning.

10. The device of claim 7, wherein the linear scanning probe comprises a gradient-index (GRIN) optics lens and two galvanometer-actuated mirrors (703), wherein the galvanometers are actuated to produce two-dimensional scanning.

11. The device of claim 1, wherein the imaging probe is rotated by an external mechanism.

12. The device of claim 1, where the treatment laser is a $CO_2$, or Er:YAG laser.

* * * * *